US010881685B2

(12) United States Patent
Gillberg et al.

(10) Patent No.: US 10,881,685 B2
(45) Date of Patent: Jan. 5, 2021

(54) CHOLESTYRAMINE GRANULES, ORAL CHOLESTYRAMINE FORMULATIONS AND USE THEREOF

(71) Applicant: Albireo AB, Gothenburg (SE)

(72) Inventors: Per-Göran Gillberg, Mölndal (SE); Nils Ove Gustafsson, Löddeköpinge (SE); Kurt Lövgren, Mölnlycke (SE)

(73) Assignee: Albireo AB, Gothenburg (SE)

( * ) Notice: Subject to any disclaimer, the term of this patent is extended or adjusted under 35 U.S.C. 154(b) by 0 days.

(21) Appl. No.: 16/125,358

(22) Filed: Sep. 7, 2018

(65) Prior Publication Data

US 2019/0070217 A1    Mar. 7, 2019

Related U.S. Application Data

(63) Continuation of application No. PCT/SE2018/050802, filed on Aug. 9, 2018.

(30) Foreign Application Priority Data

Aug. 9, 2017 (SE) .................................... 1750978

(51) Int. Cl.
| A61K 31/785 | (2006.01) |
| A61K 9/16 | (2006.01) |
| A61P 1/12 | (2006.01) |
| A61K 9/50 | (2006.01) |
| A61P 1/00 | (2006.01) |

(52) U.S. Cl.
CPC .......... *A61K 31/785* (2013.01); *A61K 9/1635* (2013.01); *A61K 9/1652* (2013.01); *A61K 9/5026* (2013.01); *A61K 9/5036* (2013.01); *A61K 9/5073* (2013.01); *A61P 1/00* (2018.01); *A61P 1/12* (2018.01)

(58) Field of Classification Search
CPC .......... A61K 31/745; A61K 9/00; A61K 9/48; A61K 45/06
See application file for complete search history.

(56) References Cited

U.S. PATENT DOCUMENTS

| 3,539,380 A | 11/1970 | Johnson |
| 4,172,120 A | 10/1979 | Todd et al. |
| 4,507,235 A | 3/1985 | Wunsch |
| 5,167,965 A | 12/1992 | Schulz |
| 5,294,448 A | 3/1994 | Ring |
| 5,350,584 A | 9/1994 | McClelland |
| 5,422,124 A | 6/1995 | Valducci |
| 5,578,316 A | 11/1996 | Bhardwaj et al. |
| 5,663,165 A | 9/1997 | Brieaddy |
| 5,681,584 A | 10/1997 | Savastano |
| 5,723,458 A | 3/1998 | Brieaddy et al. |
| 5,811,388 A | 9/1998 | Friend et al. |
| 5,817,652 A | 10/1998 | Brieaddy et al. |
| 5,900,233 A | 5/1999 | Day |
| 5,910,494 A | 6/1999 | Brieaddy |
| 5,976,811 A | 11/1999 | Mullner et al. |
| 5,994,391 A | 11/1999 | Lee et al. |
| 5,998,400 A | 12/1999 | Brieaddy et al. |
| 6,020,330 A | 2/2000 | Enhsen et al. |
| 6,069,167 A | 5/2000 | Sokol |
| 6,277,831 B1 | 8/2001 | Frick et al. |
| 6,346,527 B1 | 2/2002 | Takenaka et al. |
| 6,355,672 B1 | 3/2002 | Yasuma et al. |
| 6,387,924 B2 | 5/2002 | Lee et al. |
| 6,387,944 B1 | 5/2002 | Frick et al. |
| 6,426,340 B1 | 7/2002 | Gibson et al. |
| 6,562,860 B1 | 5/2003 | Keller et al. |
| 6,592,900 B1 | 7/2003 | Buhler |
| 6,635,280 B2 | 10/2003 | Shell et al. |
| 6,642,269 B2 | 11/2003 | Frick et al. |
| 6,676,979 B2 | 1/2004 | Marlett et al. |
| 6,784,201 B2 | 8/2004 | Lee et al. |
| 6,906,058 B2 | 6/2005 | Starke et al. |
| 6,943,189 B2 | 9/2005 | Keller et al. |
| 7,019,023 B2 | 3/2006 | Frick et al. |
| 7,125,864 B2 | 10/2006 | Starke et al. |
| 7,132,416 B2 | 11/2006 | Starke et al. |

(Continued)

FOREIGN PATENT DOCUMENTS

| CA | 2065151 | 3/1991 |
| DE | 3930168 | 3/1991 |

(Continued)

OTHER PUBLICATIONS

Fuentes-Zaragoza Resistant Starch, Food Research International. p. 931 (Year: 2010).*
"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001&rank=7, 4 pages.
"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.

(Continued)

*Primary Examiner* — Matthew P Coughlin
*Assistant Examiner* — Thurman Wheeler
(74) *Attorney, Agent, or Firm* — Fish & Richardson P.C.

(57) ABSTRACT

The invention relates to small granules comprising cholestyramine. The granules have a high cholestyramine content and are stable enough to be coated with one or more coating layers. The invention also relates to a multiparticulate drug delivery system comprising such granules. The invention further relates to an oral formulation for targeted delivery of cholestyramine to the colon, comprising a plurality of cholestyramine granules that are coated with a colon release coating. The invention also relates to the use of this formulation in the treatment of bile acid malabsorption and bile acid diarrhoea.

27 Claims, 1 Drawing Sheet

(56) References Cited

U.S. PATENT DOCUMENTS

| | | |
|---|---|---|
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,615,536 B2 | 11/2009 | Frick et al. |
| 7,767,229 B1 | 8/2010 | Milne et al. |
| 7,923,468 B2 | 4/2011 | Frick et al. |
| 7,939,061 B2 | 5/2011 | Prakash et al. |
| 7,956,085 B2 | 6/2011 | Frick et al. |
| 8,048,413 B2 | 11/2011 | Huguet |
| 8,067,584 B2 | 11/2011 | Starke et al. |
| 8,101,583 B2 | 1/2012 | Glombik et al. |
| 8,106,023 B2 | 1/2012 | Glombik et al. |
| 9,023,368 B2 | 5/2015 | Basit et al. |
| 9,295,677 B2 | 3/2016 | Ling et al. |
| 9,339,480 B2 | 5/2016 | Young et al. |
| 9,409,875 B2 | 8/2016 | Bohlin et al. |
| 9,684,018 B2 | 6/2017 | Horanzy |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anifinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0266080 A1 | 12/2005 | Desai et al. |
| 2005/0282822 A1 | 12/2005 | Alstermark et al. |
| 2006/0083790 A1 | 4/2006 | Anderberg et al. |
| 2006/0210631 A1 | 9/2006 | Patel |
| 2006/0210633 A1 | 9/2006 | Dharmadhikari |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0159087 A1 | 6/2011 | Sathe et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0052269 A1 | 2/2013 | Lescure |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2014/0275090 A1 | 9/2014 | Gedulin et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0030009 A1 | 6/2018 | Gillberg et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360869 A1 | 12/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2020/0046635 A1 | 2/2020 | Gillberg et al. |
| 2020/0046636 A1 | 2/2020 | Gillberg et al. |
| 2020/0046757 A1 | 2/2020 | Gillberg et al. |
| 2020/0046758 A1 | 2/2020 | Gillberg et al. |
| 2020/0049611 A1 | 2/2020 | Gillberg et al. |
| 2020/0140484 A1 | 5/2020 | Gillberg et al. |

FOREIGN PATENT DOCUMENTS

| | | |
|---|---|---|
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1273307 | 1/2003 |
| EP | 1535913 | 6/2005 |
| EP | 1719768 | 11/2006 |
| EP | 2144599 | 2/2008 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |
| JP | 2006/124695 | 5/2006 |
| JP | B-4870552 | 2/2012 |
| JP | 2013-541584 | 11/2013 |
| JP | 2013-542953 | 11/2013 |
| JP | A-2013-542953 | 11/2013 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/038182 | 9/1998 |
| WO | WO 1998/40375 | 9/1998 |
| WO | WO 1998/056757 | 12/1998 |
| WO | WO 1999/01149 | 1/1999 |
| WO | WO 1999/32478 | 7/1999 |

(56) References Cited

FOREIGN PATENT DOCUMENTS

| | | |
|---|---|---|
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/047568 | 8/2000 |
| WO | WO 2000/61568 | 10/2000 |
| WO | WO 2000/62810 | 10/2000 |
| WO | WO 2001/034570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/09815 | 4/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/089350 | 9/2004 |
| WO | WO 2004/020421 | 10/2004 |
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2014/174066 | 10/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |

OTHER PUBLICATIONS

"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.
"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.
"An Extension Study to Evaluate the Long-Term Safety and Durability of Effect of LUM001 in the Treatment of Cholestatic Liver Disease in Subjects With Alagille Syndrome (IMAGINE-II)," Clinical Trials.gov, Apr. 16, 2014, retrieved on Oct. 3, 2014, http://clinicaltrials.gov/ct2/show/NCT02117713?term=LUM001&rank=2, 3 pages.
"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
"EASL Clinical Practice Guidelines: Management of cholestatic liver diseases," European Assoc. for the Study of the Liver, Journal of Hepatology, 2009, 51:237-267.
"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.
"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.
"Initiation of a Phase II Trial for A4250, the Company's Lead Compound for Cholestatic Liver Diseases and Nash," Albireo Pharma Press Release, Feb. 5, 2015, http://www.alberiopharma.com/News.aspx?PageID=1600872, 2 pages.
"Lumena Pharmaceuticals Now Dosing Patients in the Indigo Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.
"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
AASLD: 2017 68th Annual Meeting of the American Association for the Study of Liver Diseases, Washington, DC, Oct. 20-24, 2017, (Abstract only).
Alissa et al., "Invited Review: Update on Progressive Familial Intrahepatic Cholestasis," *Journal of Pediatric Gastroenterology and Nutrition*, 2008, 46:241-252.
Alonso et al., "Histologic pathology of the liver in progressive familial intrahepatic cholestasis," Journal of Pediatric Gastroenterology and Nutrition, 14: 128-133, 1994.
Alvarez, Fernando; "Treatments in chronic cholestasis in children." Ann. Nestlé (2008) 66 p. 127-135.
American Diabetes Association, "Management of Dyslipidemia in Adults with Diabetes," Diabetes Care, Jan. 2003, 26(1).
Anakk et al., "Bile acids activate YAP to promote liver carcinogenesis," Cell Rep., Nov. 27, 2013, 5(4):1060-1069.

(56) References Cited

OTHER PUBLICATIONS

Angulo et al., "Independent Predictors of Liver Fibrosis in Patients With Nonalcoholic Steatohepatitis," Hepatology, Dec. 1999, 30(6): 1356-1362.

Angulo, "Use of ursodeoxycholic acid in patients with liver disease," *Current Gastroenterology Reports*, Feb. 1, 2002, 4(1):37-44.

Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.

Artursson and Karlsson, "Correslation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.

Attili et al., "Bile Acid-induced Liver Toxicity: Relation to the Hydrophobic-Hydrophilic Balance of Bile Acids," Medical Hypotheses, 1986, 19:57-69.

Baghdasaryan et al., "Inhibition of intestinal bile acid absorption by ASBT inhibito A4250 protects against bile acid-mediated cholestatic liver injury in mice," J. Hepatology, 2014, 60:S57.

Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.

Bajor et al., "Bile acids: short and long term effects in the intestine," Scandanavian J. Gastro., 2010, 45:645-664.

Balbach et al., "Pharmaceutical evaluation of early development candidates "The 100 mg-approach"," Int J Pharm, May 4, 2004, 275(1):1-12.

Banker et al., "Modern Pharmaceutics, 3ed", Marcel Dekker, New York, 1996, pp. 451 and 596.

Baumann, U. et al., "The ileal bile acid transport inhibitor A4250 decreases pruritus and serum bile acids in cholestatic liver diseases— an ongoing multiple dose, open-label, multicenter study," Hepatology, 2017, 66(1): S91 (Abstract only).

Bavin, "Polymorphism in Process Development," Chemistry and Industry, 527-529, 1989.

Beraza et al., Nor-ursodeoxycholic acid reverses hepatocyte-specific nemo-dependnt steatohepatitis. Gut, 2011: 60: 387-396.

Billington et al., "Effects of bile salts on the plasma membranes of isolated rat hepatocytes," Bichem. J. 188: 321-327, 1980.

Board of Appeal of European Patent Office, Case No. T 077/08-3. 3.01, dated May 24, 2011, 17 pages.

Bonge et al., "Cytostar-T Scintillating Microplate Assay for Measurement of Sodium-Dependent Bile Acid Uptake in Transfected HEK-293 Cells," Analytical Biochemistry, 2000, 282:94-101.

Brunt et al., "Nonalcoholic Steatohepatitis: A Proposal for Grading and Staging the Histological Lesions," American Jounral of Gastroenterology, Sep. 1999, 94(9): 2467-2474.

Brunzell and Hokanson, "Dislipidemia of Central Obesity and Insulin Resistance," Diabetes Care, 1999, 22(Suppl. 3):C10-C13.

Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.

Byrn et al., "Pharmaceutical Solids: A Strategic Approach to Regulatory Considerations," Pharmaceutical Research, 1995, 12(7), pp. 945-954.

Caira, "Crystalline Polymorphism of Organic Compounds," in: Topics in Current Chemistry, Jan. 1998, 198:163-208.

Carulli et al, "Review article: effect of bile salt pool composition on hepatic and biliary functions," Aliment. Pharmacol. Ther. 2000, vol. 14, suppl. 2, p. 14-18.

Chen et al., "Bile salt export pump is dysregulated with altered farnesoid X receptor isoform expression in patients with hepatocelular carcinoma," Hepatologu, 57: 4, 1530-1541, 2013.

Chen et al., "Inhibition of apical sodium-dependent bile acid transporter as a novel treatment for diabetes," Am J Physiol Endocrinol Metab, 2012, 302:E68-E76.

Chen et al., "Progressive Familial Intrahepatic Cholestasis, Type 1, is Associated with Decreased Farnesoid X Receptor Activity," Gastroenterology, 2004, 126:756-764.

Chen et al., "Serum and urine metabolite profiling reveals potential biomarkers of human hepatocellular carcinoma," Molecular and Cellular Proteomics 10.7, 2011.

Chey et al., "A Randomized Placebo-Controlled Phase II b Trial of A3309, a Bile Acid Transporter Inhibitor, for Chronic Idiopathic Constipation," Am. J. Gastroenterology, May 2011, 106:1803-1812.

Chourasia et al., "Polysaccharides for colon targeted drug delivery," Drug Delivery, Academic Press, vol. 11, No. 2, Jan. 1, 2004, 129-148, XP008060983.

Das & Kar., Non alcoholic steatohepatitis. JAPI. 53:, Mar. 2005.

Dashti et al., "A Phospholipidomic Analysis of All Defined Human Plasma Lipoproteins," Nature.com: Scientific Reports, Nov. 2011, DOI: 10.1038, 11 pages.

Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease*, May 2010, 1645-1655.

Davit-Spraul et al., "Progressive familial intrahepatic cholestasis," *Orphanet Journal of Rare Diseases*, Jan. 2009, 4:1-12.

Dawson et al., "Bile acid transporters" J. Lipid Res. 2009, 50, 2340-2357.

DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.

Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).

DiBaise et al., "Bile Acids: An Underrecognized and Underappreciated Cause of Chronic Diarrhea", Pract. Gastroenterol. vol. 36(10), p. 32-44, 2012.

Dongiovanni et al., "Genetic Predisposition in NAFLD and NASH: Impact on Severity of Liver Disease and Response to Treatment," Curren Pharma Design, 2013, 19:5219-5238.

Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.

Espenshade and Hughes, "Regulation of Sterol Synthesis in Eukaryotes," Annu. Rev. Genet., 2007, 41:401-427.

Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.

Extended European Search Report in European Application No. 11840392.2, dated Feb. 24, 2014, 7 pages.

Extended European Search Report in European Application No. 11840481.3, dated Feb. 13, 2014, 10 pages.

Faubion et al., "Toxic bile salts induce rodent hepatocyte apoptosis via direct activation of Fas," The Journal of Clinical Investigation, 103: 1, 137-145, 1999.

Forner et al., "Treatment of hepatocellular carcinoma," Critical Reviews in Oncology/Hematology, 2006, 60:89-98.

Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.

Gillberg et al., "The IBAT Inhibition by A3309—A Potential Mechanism for the Treatment of Constipation," Gastroenterology, 2010, 138(5), Supp 1, S-224.

(56) References Cited

OTHER PUBLICATIONS

Glasgov et al., "Compensatory enlargement of human atherschlerotic coronary arteries," N. Engl. J. Med., May 1987, 316(22):1371-1375 (Abstract Only).
Govers et al., "Characterization of the adsorption of conjugated and unconjugated bile acids to insoluble, amorphous calcium phosphate", Journal of Lipid Research 35(5):741-748, 1994.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Heathcote, "Management of primary biliary cirrhosis," Hepatology, 2000, 31(4):1005-1013.
hepc.liverfoundation.org' [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Hollands et al., "Ileal exclusion for Byler's disease: an alternative surgical approach with promising early results for pruritis,"Journal of Pediatric Surgery, Feb. 1988, 33(2): 220-224.
Huang et al., "Discovery of Potent, Nonsystemic Apical Sodium-Codependent Bile Acid Transporter Inhibitors (Part 2)," J. Med. Chem., 2005, 48:5853-5868.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dated May 8, 2017, 16 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12pages.
International Search Report and Written Opinion for International Application No. PCT/SE2011/051336, dated Feb. 22, 2012, 18 pages.
International Search Report and Written Opinion in International Application No. PCT/SE2018/050802, dated Oct. 26, 2018.
International Search Report and Written Opinion in International Application No. PCT/SE2018/050803, dated Oct. 26, 2018.
International Search Report, Application No. PCT/JP2015/068240, dated Sep. 15, 2015, 11 pages (with English translation).
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise, "Bile Acids: An underrecognized and underappreciated cause of chronic diarrhea," Pract. Gastroenterol. 2012, vol. 36(10), p. 32-44.
Jacobsen et al., "Effect of enterocoated cholestyramine on bowel habit after ileal resection: a double blind crossover study," Br. Med. J. 1985, vol. 290, p. 1315-1318.
Jacquet et al., "Alagille Syndrome in Adult Patients: It is Never Too Late," *American Journal of Kidney Diseases*, May 2007, 49(5):705-709.
Jansen et al., "Endogenous bile acids as carcinogens," Journal of Hepatology, Sep. 2007, 47(3):434-435.
Jiang et al., "Non alcoholic steatohepatitis a precursor for hepatocellular carcinoma development," World Journal of Gastroenterology: WJG, Nov. 28, 2014, 20(44):16464-16473.
Knisely et al., "Hepatocellular Carcinoma in ten children under five years of age with bile salt export pump deficiency," Hepatology, Aug. 2006, 44(2):478-486.
Korman et al., "Assessment of Activity in Chronic Active Liver Disease," New England Journal of Medicine, 2010, 290(25):1399-1402.
Kumar and Tandon, "Use of ursodeoxycholic acid in liver diseases," J. Gastroenterology and Hepatology, 2001, 16:3-14.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Kurbegov et al., Biliary diversion for progressive familial intrahepatic cholestasis: Improved liver morphology and bile acid profile, Gastroenterology, 125: 4, 1227-1234, 2003.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lewis et al., "Effects of 2164U90 on ileal bile acid adsorption and serum cholesterol in rats and mice", Journal of Lipid Research 36(5):1098-1105, 1995.
Ling, "Congenital cholestatic syndromes: What happens when children grow up?," Can J Gastroenterol, Nov. 11, 2007, 21(11):743-751.
Longo et al., "Hyperlipidemia in chronic cholestatic liver disease," Curr. Treat. Options Gastrenterol., 2001, 4:111-114.
Lykavieris et al., "Outcome of liver disease in children with Alagille syndrome: a study of 163 patients," *Gut*, 2001, 49:431-435.
Marzorati et al, "A novel hypromellose capsule, with acid resistance properties, permits the targeted delivery of acid-sensitive products to the intestine, " LWT-Food Sci. Techno.1 2015, vol. 60, p. 544-551.
McCullough et al., "The epidemiology and risk factors of NASH.", Blackwell Publishing, Chapter 3, 2005.
MerckManuals com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Morissette et al., "High-throughput crystallization: pharmaceutical solids," Advanced Drug polymorphs, salts, co-crystals and solvates of Delivery Reviews, 2004, 56:275-300.
Mouzaki and Allard, "Non-alcoholic steatohepatitis: the therapeutic challenge of a global epidemic," Annals of Gastroenterology, 2012, 25: 207-217.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Okubo et al., "II, Daihyoteki Shikkan no Shinryo to Genkyo to Shorai Tenbo 6, Nanjisei Benpi," The Journal of the Japanese Society of Internal Medicine Jan. 10, 2013 (Jan. 10, 2013), 102(1), pp. 83-89.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.

(56) References Cited

OTHER PUBLICATIONS

Pattni and Walters, "Recent advances in the understanding of bile acid malabsorption," Br. Med. Bull. 2009, vol. 92, p. 79-93.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Possemiers et al, "PCR-DGGE-based simulator of the human intestinal microbial quantification of stability of the microbial community in a ecosystem," FEMS Microbiol. Ecol. 2004, vol. 49, p. 495-507.
Poupon et al., "Chronic Cholestatic Disease," J. Hepatology, 2000, 32(1):12-140.
Qiu et al., "Disruption of BSEP function in HepaRG cells alters bile acid disposition and is a susceptive factor to drug-induced cholestatic injury," Mol. Pharmaceutics, 13:4 2016 (Abstract only).
Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Rolo et al., "Bile acids affect liver mitochondrial bioenergetics: Possible relevance for cholestasis therapy," Toxocological Sciences, 57: 177-185, 2000.
Satapathy and Sanyal, "Epidemiology and Natural History of Nonalcoholic Fatty Liver Disease," Seminars in Liver Disease, Aug. 2015, 35(3): 221-235.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Shah et al., "Role of Caco-2 Cell Monolayers in Prediction of Intestinal Drug Absorption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Singhal et al., "Drug polymorphism and dosage form design: a practical perspective," Adv Drug Deliv Rev, Feb. 23, 2004, 56(3):335-347.
Sinha and Kumria, "Microbially triggered drug delivery to the colon," Eur. J. Pharm. Sci. 2003, vol. 18, p. 3-18.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Staels and Kuipers, "Bile Acid Sequestrants and the Treatment of Type 2 Diabetes Mellitus," Drugs, 2007, 67(10):1383-1392.
Stein, "Managing Dyslipidemia in the High-Risk Patient," Am J. Cardiol., 2002, 89:50-57.
Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.
Tanaka et al., "Genetic and Familial considerations of Primary Biliary Cirrhosis," Am. J. Gastroenterology, 2001, 96(1): 8-15.
Tollefson et al., "A novel class of apical sodium co-dependent bile acid transporter inhibitors: the 1,2-Benzothiazepines", Bioorganic and Medicinal Chemistry Letters 12:3727-3730, 2003.
Tremont et al., "Discovery of Potent, Nonsystemic Apical Sodium-Codependent Bile Acid Transporter Inhibitors (Part 1)," J. Med. Chem, 2005, 48:5837-5852.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Tilberg et al., "Na+-dependent bile acid transport in the ileum: the balance between diarrhea and constipation", Gastroenterology 98(1):25-32, 1989.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Watts and Ilium, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
Whitington et al., "Partial external diversion of bile for the treatment of intractable pruitus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Woolbright et al., "Novel insight into mechanisms of cholestatic liver injury," World Journal of Gastroenterology, 18: 36, 4985-4993, 2012.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zhang et al., "Effect of bile duct ligation on bile acid composition in mouse serum and liver," Liver int, 32: 1, 58-69, 2012.
Zhang et al., Abcb11 deficiency induces cholestasis coupled to impaired B-Fatty acid oxidation in mice, Journal of biological chemistry, 287: 29, 24784-2479, 2012.
Bhaskaran et al. Extrusion Spheronization—A Review. International Journal of PhamnTech Research.vol. 2, No. 4, pp. 2429-2433, Oct.-Dec. 2010 (Year: 2010).
Burrows, "Interventions for treating cholestasis in pregnancy," Cochrane Database Syst. Rev., 4:CD00493, 2001.
Camilleri, "Probiotics and irritable bowel syndrome: rationale, putative mechanisms, and evidence of clinical efficacy," Clin. Gastroenterol., 40(3):264-9, Mar. 2006.
Chen et al., "Treatment effect of rifampicin on cholestasis," Internet Journal of Pharmacology, 4(2), 2006.
Chen et al., "The effects of diets enriched in beta-glucans on blood lipoprotein concentrations," J. Clin. Lipidol., 3(3):154-8, May 2009.
Centeno, "Molecular mechanisms triggered by low-calcium diets," Nutrition research reviews., 22(2):163-74, Dec. 2009.
Einspahr et al., "Protective role of wheat bran fiber: data from marker trials," Am. J. Med., 106(1A):32s-37s, Jan. 1999.
Jankowska et al., "[Cholestatic liver disease in children]," Przegl. Epidemiol., 56:16-21, 2002.
Li et al., "Effect of Resistant Starch Film Properties on the Colon-Targeting Release of Drug From Coated Pellets", 152 J Control. Rel. e5, 2011.

(56) References Cited

OTHER PUBLICATIONS

Manghat and Wierzbicki, "Colesevelam hydrochloride: a specifically engineered bile acid sequestrant," Future Lipidology, 3(3):237-255, Jun. 2008.
McMichael and Potter, "Reproduction, endogenous and exogenous sex hormones, and colon cancer: a review and hypothesis," J. Natl. Cancer Inst., 65(6):1201-07, Dec. 1980.
Mowat et al., "Respiratory chain complex III [correction of complex] in deficiency with pruritus: a novel vitamin responsive clinical feature," J. Pediatr., 134(3):352-4, Mar. 1999.
O'Neill et al.,"Comparison of efficacy of plant stanol ester and sterol ester: short-term and longer-term studies," American Journal of Cardiology, 96(1A):29d-36D, Jul. 2005.
Pai et al. Compression and evaluation of extended release matrix pellets prepared by the extrusion/spheronization process into disintegrating tablets. Brazilian Journal of Pharmaceutical Sciences. vol. 48, n. 1 janinnar., 2012 (Year: 2012)
Renga et al., "Role of FXR in regulating bile acid homeostasis and relevance for human diseases," Curr. Drug. Targets Immune Endocr. Metabol. Disord., 5(3):289-303, Sep. 2005.
Sanyal et al. The etiology of hepatocellular carcinonna and consequences of treatment. The Oncologist, 2010, 15 Suppl 4, 14-22.
Schumpelick et al., "[Ulcerative colitis—late functional results of ileoanal pouch anastomosis]," Chirung, 69(10):1013-19, Oct. 1998.
Simons, "The fate of the orally administered bile acid sequestrant, polidexide, in humans," Clin. Exp. Pharmacol. Physiol., 3(1):99-101, Jan.-Feb. 1976.
Sirtori, "Mechanisms of lipid-lowering agents," Cardiology, 78(3):226-35, 1991.
Staels and Kuipers, "Bile acid sequestrants and the treatment of type 2 diabetes mellitus," Drugs, 67(10):1383-92, 2007.
Suzuki and Takada, "Mechanisms of regulation of bile acid transport in the small intestine," Falk Symposium, 165:76-81, 2009.
Walkowiak-Tomczak, "Characteristics of plums as a raw material with valuable nutritive and dietary properties—a review," Pol. J. Food Nutr. Sci., 58(4):401-405, 2008.
Kolter et al., "Structure and dry binding activity of different polymers, including Kollidon VA 64," Drug Development, 2000, 26(11):1159-65.
Neuvonen et al., "Activated charcoal in the treatment of hypercholesterolaemia: dose-response relationships and comparison with cholestyramine," Eur J Clin Pharnnacol, 1989, 37(3):225.
International Search Report and Written Opinion in International Appln. No. PCT/EP2020/052940, dated Mar. 23, 2020, 12 pages.
International Search Report and Written Opinion in International Appln. No. PCT/EP2020/052942, dated Mar. 23, 2020, 9 pages.

* cited by examiner

CHOLESTYRAMINE GRANULES, ORAL CHOLESTYRAMINE FORMULATIONS AND USE THEREOF

CROSS-REFERENCE TO RELATED APPLICATIONS

This application is a Continuation under 35 U.S.C. § 111(a) of International Application No. PCT/SE2018/050802, filed Aug. 9, 2018, which claims priority to SE Application No. 1750978-7, filed Aug. 9, 2017.

The invention relates to small granules comprising cholestyramine. The granules have a high cholestyramine content and are stable enough to be coated with one or more coating layers. The invention also relates to a multiparticulate drug delivery system comprising such granules. The invention further relates to an oral formulation for targeted delivery of cholestyramine to the colon, comprising a plurality of cholestyramine granules that are coated with a colon release coating. The invention also relates to the use of this formulation in the treatment of bile acid malabsorption and bile acid diarrhoea.

BACKGROUND

Bile acid malabsorption is a condition characterized by an excess of bile acids in the colon, often leading to chronic diarrhoea. Bile acids are steroid acids that are synthesized and conjugated in the liver. From the liver, they are excreted through the biliary tree into the small intestine where they participate in the solubilisation and absorption of dietary lipids and fat-soluble vitamins. When they reach the ileum, bile acids are reabsorbed into the portal circulation and returned to the liver. A small proportion of the secreted bile acids is not reabsorbed in the ileum and reaches the colon. Here, bacterial action results in deconjugation and dehydroxylation of the bile acids, producing the secondary bile acids deoxycholate and lithocholate.

In the colon, bile acids (in particular the dehydroxylated bile acids chenodeoxycholate and deoxycholate) stimulate the secretion of electrolytes and water. This increases the colonic motility and shortens the colonic transit time. If present in excess, bile acids produce diarrhoea with other gastrointestinal symptoms such as bloating, urgency and faecal incontinence. There have been several recent advances in the understanding of this condition of bile salt or bile acid malabsorption, or BAM (Pattni and Walters, *Br. Med. Bull.* 2009, vol 92, p. 79-93; Islam and Di Baise, *Pract. Gastroenterol.* 2012, vol. 36(10), p. 32-44). Dependent on the cause of the failure of the distal ileum to absorb bile acids, bile acid malabsorption may be divided into Type 1, Type 2 and Type 3 BAM. Diarrhoea may also be the result of high concentrations of bile acid in the large intestine following treatment with drugs that increase the production of bile acids and/or influence the reabsorption of bile acids by the small intestine, such as treatment with ileal bile acid absorption (IBAT) inhibitors.

The current treatment of bile acid malabsorption aims at binding excess bile acids in the gastrointestinal tract, beginning in the proximal part of the small bowel, thereby reducing the secretory actions of the bile acids. For this purpose, cholestyramine is commonly used as a bile acid sequestrant. Cholestyramine (or colestyramine; CAS Number 11041-12-6) is a strongly basic anion-exchange resin that is practically insoluble in water and is not absorbed from the gastrointestinal tract. Instead, it absorbs and combines with the bile acids in the intestine to form an insoluble complex. The complex that is formed upon binding of the bile acids to the resin is excreted in the faeces. The resin thereby prevents the normal reabsorption of bile acids through the enterohepatic circulation, leading to an increased conversion of cholesterol to bile acids to replace those removed from reabsorption. This conversion lowers plasma cholesterol concentrations, mainly by lowering of the low-density lipoprotein (LDL)-cholesterol.

Cholestyramine is also used as hypolipidaemic agents in the treatment of hypercholesterolemia, type II hyperlipoproteinaemia and in type 2 diabetes mellitus. It is furthermore used for the relief of diarrhoea associated with ileal resection, Crohn's disease, vagotomy, diabetic vagal neuropathy and radiation, as well as for the treatment of pruritus in patients with cholestasis.

In the current treatment of hyperlipidaemias and diarrhoea, the oral cholestyramine dose is 12 to 24 g daily, administered as a single dose or in up to 4 divided doses. In the treatment of pruritus, doses of 4 to 8 g are usually sufficient. Cholestyramine may be introduced gradually over 3 to 4 weeks to minimize the gastrointestinal effects. The most common side-effect is constipation, while other gastrointestinal side-effects are bloating, abdominal discomfort and pain, heartburn, flatulence and nausea/vomiting. There is an increased risk for gallstones due to increased cholesterol concentration in bile. High doses may cause steatorrhoea by interference with the gastrointestinal absorption of fats and concomitant decreased absorption of fat-soluble vitamins. Chronic administration may result in an increased bleeding tendency due to hypoprothrombinaemia associated with vitamin K deficiency or may lead to osteoporosis due to impaired calcium and vitamin D absorption. There are also occasional reports of skin rashes and pruritus of the tongue, skin and perianal region. Due to poor taste and texture and the various side effects, >50% of patients discontinue therapy within 12 months.

Another drawback with the current treatment using cholestyramine is that this agent reduces the absorption of other drugs administered concomitantly, such as oestrogens, thiazide diuretics, digoxin and related alkaloids, loperamide, phenylbutazone, barbiturates, thyroid hormones, warfarin and some antibiotics. It is therefore recommended that other drugs should be taken at least 1 hour before or 4 to 6 hours after the administration of cholestyramine. Dose adjustments of concomitantly taken drugs may still be necessary to perform.

In view of these side effects, it would be desirable if cholestyramine could be formulated as a colon release formulation, i.e. for release of the cholestyramine in the proximal part of the colon. Such a formulation may require a lower dose of cholestyramine and should have better properties regarding texture and taste, and may therefore be better tolerated by the patients. More importantly, colonic release of cholestyramine should be devoid of producing interactions with other drugs and should not induce risks for malabsorption of fat and fat-soluble vitamins, while still binding bile acids in order to reduce the increased colonic secretion and motility. For reasons of patient compliance, it would furthermore be desirable if the number of pills to be taken could be kept as low as possible. Each pill should therefore contain as much cholestyramine as possible.

EP 1273307 discloses preparations for preventing bile acid diarrhoea, comprising a bile acid adsorbent coated with a polymer so as to allow the release of the bile acid adsorbent around an area from the lower part of the small intestine to the cecum. It is shown that cholestyramine granules coated with HPMCAS-HF or ethyl cellulose displayed extensive swelling and bursting under conditions simulating the gastric environment.

Jacobsen et al. (*Br. Med. J.* 1985, vol. 290, p. 1315-1318) describe a study wherein patients who had undergone ileal resection were administered 500 mg cholestyramine tablets coated with cellulose acetate phthalate (12 tablets daily). In five of the 14 patients in this study, the tablets did not disintegrate in the desired place.

WO 2017/138876 discloses cholestyramine pellets comprising at least 70% cholestyramine. These pellets contain lower amounts of a vinylpyrrolidone-based polymer as the binding agent.

WO 2017/138877 and WO 2017/138878 disclose oral formulations for targeted delivery of cholestyramine to the colon, which formulations comprise a plurality of coated cholestyramine pellets.

Despite progress made in this area, there still is a need for further improved cholestyramine formulations. In particular, there is a need for small cholestyramine particles that have a high cholestyramine content and are stable during the coating process.

SUMMARY OF THE INVENTION

The invention provides small and stable granules that have a cholestyramine content of at least 70% and that are stable enough to withstand the conditions conventionally used for applying one or more coating layers. In particular, the invention provides a population of granules, each granule comprising at least 70% w/w cholestyramine and
i. at least 7% w/w of a binding agent; or
ii. a combination of at least 6% w/w of a binding agent and at least 2% w/w of an acrylate copolymer; or
iii. a combination of at least 5% w/w of a binding agent and at least 3% w/w of an acrylate copolymer; or
iv. a combination of at least 6% w/w of a binding agent, at least 1% w/w of an acrylate copolymer and from 5% to 15% w/w of microcrystalline cellulose.

The granules can be coated with one or more coating layers that prevent release of the cholestyramine until the granules reach the colon.

In another aspect, the invention provides a multiparticulate drug delivery system comprising a plurality of cholestyramine granules as described herein, more particularly a drug delivery system wherein the cholestyramine granules are formulated for colon targeted delivery.

In yet another aspect, the invention provides an oral formulation for targeted delivery of cholestyramine to the colon, comprising a plurality of granules as described herein and a colon release coating around said granules. The combination of small cholestyramine granules and a colon release coating allows the dose of cholestyramine to be reduced to for example 1.5 g twice daily. It is believed that this dose of cholestyramine is sufficient for binding an excess of bile acids in the colon. The formulation may therefore be used in the treatment or prevention of bile acid malabsorption and bile acid diarrhoea.

BRIEF DESCRIPTION OF THE DRAWINGS

FIG. 1A shows the results for formulations A, B and C during 6 hours at pH 5.5. FIG. 1B shows the results for formulations A, B and C during 2 hours at pH 1 followed by 4 hours at pH 6.8.

DETAILED DESCRIPTION OF THE INVENTION

Figure 1A:
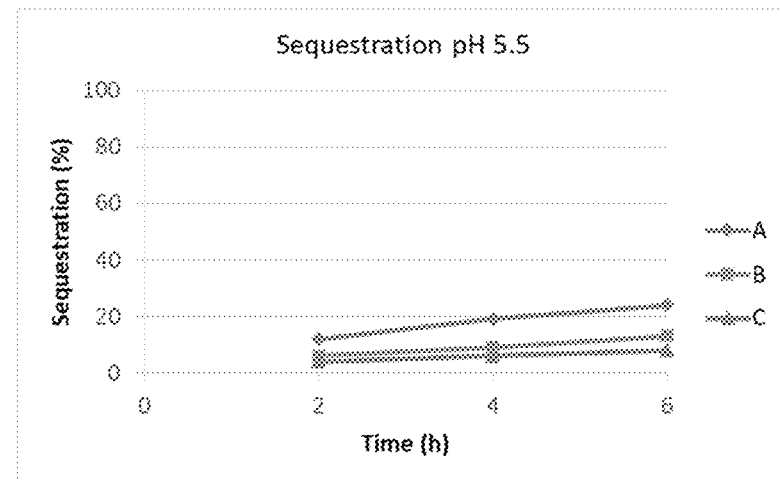
FIGS. 1A and 1B shows the sequestration profiles for different formulations in an assay simulating the pH of the stomach and the small intestine.

It has been discovered that small and stable granules of cholestyramine can be obtained by granulating a mixture comprising cholestyramine and an appropriate binding agent. Such granules have a high cholestyramine content and are stable enough to withstand the conditions conventionally used for applying one or more coating layers.

In a first aspect, the invention relates to a population of granules, each granule comprising at least 70% w/w cholestyramine, and
i. at least 7% w/w of a binding agent; or
ii. a combination of at least 6% w/w of a binding agent and at least 2% w/w of an acrylate copolymer; or
iii. a combination of at least 5% w/w of a binding agent and at least 3% w/w of an acrylate copolymer; or
iv. a combination of at least 6% w/w of a binding agent, at least 1% w/w of an acrylate copolymer and from 5% to 15% w/w of microcrystalline cellulose;
wherein the binding agent comprises an agent selected from the group consisting of cellulose ethers, vinylpyrrolidone-based polymers, sucrose, lactose, carrageenan, starch, alginic acid, sodium alginate, glyceryl behenate, polyethylene oxide, chitosan, carnuba wax, gelatin, acacia, guar gum and polyvinyl alcohol-polyethylene glycol-graft-co-polymer, or a combination thereof.

As used herein, the term "granules" refers to granules obtained through wet granulation.

It is essential that the granules are stable enough to withstand mechanical stress during handling, such as during drying and coating of the granules. The stability of the granules may be expressed in terms of friability, which is the ability of a solid substance (such as a tablet, granule, sphere or pellet) to be reduced to smaller pieces, e.g. by abrasion, breakage or deformation. A low degree of friability means that the solid substance breaks into smaller pieces only to a low extent. As used herein, friability is defined as the reduction in the mass of the granules occurring when the granules are subjected to mechanical strain, such as tumbling, vibration, fluidization, etc. Methods for measuring friability are known in the art (e.g., European Pharmacopoeia 8.0, test 2.9.41).

The inclusion of smaller amounts of binding agent and/or acrylate copolymer than specified above results in lower yield and higher friability of the granules. The friability is preferably less than 3.5%, such as less than 3.0%, such as less than 2.5%, or such as less than 2.0%, more preferably less than 1.5%, even more preferably less than 1.0%, and yet even more preferably less than 0.5%.

In a preferred embodiment, the invention relates to a population of granules, each granule comprising at least 70% w/w cholestyramine, and
i. at least 7% w/w of a binding agent; or
ii. a combination of at least 6% w/w of a binding agent and at least 2% w/w of an acrylate copolymer; or
iii. a combination of at least 5% w/w of a binding agent and at least 3% w/w of an acrylate copolymer; or
iv. a combination of at least 6% w/w of a binding agent, at least 1% w/w of an acrylate copolymer and from 5% to 15% w/w of microcrystalline cellulose;
wherein the binding agent comprises a cellulose ether, a vinylpyrrolidone-based polymer, or a combination thereof.

The cellulose ether may be any cellulose ether that is suitable for pharmaceutical and oral use. Examples of suitable cellulose ethers include methyl cellulose; ethyl cellulose; ethyl methyl cellulose; ethyl hydroxyethyl cellulose (ethulose); hydroxyethyl cellulose; hydroxyethyl methyl cellulose; hydroxypropyl cellulose (HPC); hydroxypropyl methylcellulose (HPMC or hypromellose); carboxymethyl cellulose (CMC) or the sodium salt thereof (NaCMC); and mixtures comprising two or more of the aforementioned cellulose ethers.

The vinylpyrrolidone-based polymer may be polyvinylpyrrolidone (povidone) or a vinylpyrrolidone-vinyl acetate copolymer (copovidone). Povidone is a linear, water-soluble polymer made from N-vinylpyrrolidone. Copovidone (also known as copolyvidone) is a linear, water-soluble copolymer of 1-vinyl-2-pyrrolidone (povidone) and vinyl acetate in a ratio of 6:4 by mass. In a preferred embodiment, the vinylpyrrolidone-based polymer is copovidone.

In one embodiment, the binding agent is a cellulose ether (i.e., the binding agent does not comprise a vinylpyrrolidone-based polymer). The cellulose ether is preferably methyl cellulose, hydroxypropylcellulose, hydroxypropyl methylcellulose or sodium carboxymethyl cellulose, or a mixture comprising two or more of these cellulose ethers.

In another embodiment, the binding agent is a vinylpyrrolidone-based polymer (i.e., the binding agent does not comprise a cellulose ether). The vinylpyrrolidone-based polymer is preferably copovidone.

In yet another embodiment, the binding agent comprises both a cellulose ether and a vinylpyrrolidone-based polymer. The cellulose ether is preferably methyl cellulose, hydroxypropylcellulose, hydroxypropyl methylcellulose or sodium carboxymethyl cellulose, or a mixture comprising two or more of these cellulose ethers, and the vinylpyrrolidone-based polymer is preferably copovidone.

The acrylate copolymer may be any pharmaceutically acceptable copolymer comprising acrylate monomers. Examples of acrylate monomers include, but are not limited to, acrylate (acrylic acid), methyl acrylate, ethyl acrylate, methacrylic acid (methacrylate), methyl methacrylate, butyl methacrylate, trimethylammonioethyl methacrylate and dimethylaminoethyl methacrylate. Several acrylate copolymers are known under the trade name Eudragit®.

Poly(ethyl acrylate-co-methyl methacrylate-co-trimethylammonioethyl methacrylate chloride) is a copolymer of ethyl acrylate, methyl methacrylate and a low content of trimethylammonioethyl methacrylate chloride (a methacrylic acid ester with quaternary ammonium groups). The copolymer is also referred to as ammonio methacrylate copolymer. It is insoluble but the presence of the ammonium salts groups makes the copolymer permeable. The copolymer is available as a 1:2:0.2 mixture (Type A) or as a 1:2:0.1 mixture (Type B). 30% aqueous dispersions of Type A and Type B are sold under the trade names Eudragit® RL 30 D and Eudragit® RS 30 D, respectively.

Poly(methyl acrylate-co-methyl methacrylate-co-methacrylic acid) 7:3:1 is a copolymer of methyl acrylate, methyl methacrylate and methacrylic acid. It is insoluble in acidic media but dissolves by salt formation above pH 7.0. A 30% aqueous dispersion is sold under the trade name Eudragit® FS 30 D. Poly(methacrylic acid-co-ethyl acrylate) 1:1 is a copolymer of ethyl acrylate and methacrylic acid. It is insoluble in acidic media below a pH of 5.5 but dissolves above this pH by salt formation. A 30% aqueous dispersion is sold under the trade name Eudragit® L 30 D-55.

Further suitable acrylate copolymers include poly(ethyl acrylate-co-methyl methacrylate) 2:1, which is a water-insoluble copolymer of ethyl acrylate and methyl methacrylate. 30% aqueous dispersions are sold under the trade names Eudragit® NE 30 D and Eudragit® NM 30 D.

Preferred acrylate copolymers are ammonio methacrylate copolymer, poly(methyl acrylate-co-methyl methacrylate-co-methacrylic acid) 7:3:1, and poly(methacrylic acid-co-ethyl acrylate) 1:1. More preferably, the acrylate polymer is ammonio methacrylate copolymer, and most preferably the acrylate polymer is poly(ethyl acrylate-co-methyl methacrylate-co-trimethylammonioethyl methacrylate chloride) 1:2:0.2.

Granules according to alternatives i-iii may further comprise an excipient such as microcrystalline cellulose. Microcrystalline cellulose, or MCC, is a purified, partly depolymerised cellulose with shorter, crystalline polymer chains. Its binding performance makes MCC one of the most commonly used fillers and binders in drug formulations. In one embodiment, granules according to alternatives i-iii comprise up to 10% w/w of microcrystalline cellulose, such as 1, 2, 3, 4, 5, 6, 7, 8, 9 or 10% w/w of microcrystalline cellulose. In another embodiment, granules according to alternatives i-iii comprise up to 5% w/w of microcrystalline cellulose. In another embodiment, granules according to alternatives i-iii are free of microcrystalline cellulose.

Granules according to alternative iv comprise from 5% to 15% w/w of microcrystalline cellulose, and preferably comprise at least 10% w/w of microcrystalline cellulose, i.e. 10, 11, 12, 13, 14 or 15% w/w of microcrystalline cellulose.

The granules are sieved to obtain a granule fraction with a suitable size distribution. The diameter of the cholestyramine granules is preferably from 500 μm to 3000 μm, more preferably from 750 μm to 2000 μm and even more preferably from 1000 to 1600 μm. In a most preferred embodiment, the diameter of the granules is from 1000 to 1400 μm.

Because of its physical nature, cholestyramine powder is able to absorb large amounts of water, which results in considerable swelling of the material. In order to prepare a wet mass from dry cholestyramine, it is therefore necessary to add more water than normally would be used for preparing a wet mass from dry ingredients. Preferably, water is added to the mix of dry ingredients in an amount of at least 1.5 times the amount of cholestyramine (w/w), more preferably in an amount of at least 1.75 times the amount of cholestyramine (w/w), and even more preferably in an amount of at least 2 times the amount of cholestyramine (w/w).

The uncoated granules rapidly disintegrate under aqueous conditions. However, they are stable enough to withstand the conditions necessary for applying one or more coating layer onto the granules.

Since the cholestyramine granules should bind excess bile acids in the colon, they should be formulated for colon targeted delivery. This can be achieved by coating the cholestyramine granules with one or more layers that delay the release of the cholestyramine until the granules have reached the colon.

Therefore, in another aspect, the invention relates to a multiparticulate drug delivery system comprising a plurality of cholestyramine granules as described herein. In a preferred embodiment, the cholestyramine granules are formulated for colon targeted delivery. The granules are then coated with one or more coating layers that delay release of the cholestyramine from the granules until the coated granules have reached the large intestine, in particular the proximal colon. In one embodiment, the colon targeted delivery is based on an enzyme-controlled release of the granules.

In another embodiment, the colon targeted delivery is based on a pH- and diffusion-controlled release of the granules.

Because of its very low solubility, cholestyramine is not "released" from a formulation comprising coated cholestyramine granules in that it dissolves from the formulation and diffuses into the intestine. Instead, the cholestyramine probably stays within the gradually degrading structure of the coated granule. Therefore, as used herein, the term "release" of the cholestyramine refers to the availability of the cholestyramine to the intestinal content in order to bind components (i.e., bile acids) therein.

In another aspect, the invention relates to an oral formulation for targeted delivery of cholestyramine to the colon, comprising
  a) a plurality of granules as disclosed herein; and
  b) a colon release coating around said granules.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein more than 70% of the cholestyramine is released in the colon.

In some embodiments, more than 75% of the cholestyramine is released in the colon. In other embodiments, more than 80% of the cholestyramine is released in the colon. In other embodiments, more than 85% of the cholestyramine is released in the colon. In yet other embodiments, more than 90% of the cholestyramine is released in the colon.

In yet another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein less than 30% of the cholestyramine is released in the small intestine.

In some embodiments, less than 25% of the cholestyramine is released in the small intestine. In other embodiments, less than 20% of the cholestyramine is released in the small intestine. In other embodiments, less than 15% of the cholestyramine is released in the small intestine. In yet other embodiments, less than 10% of the cholestyramine is released in the small intestine.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein the granules exhibit a friability of less than 3.5% as measured using the European Pharmacopoeia 8.0, test 2.9.41.

In some embodiments, the granules exhibit a friability of less than 3.0%. In other embodiments, the granules exhibit a friability of less than 2.5%. In other embodiments, the granules exhibit a friability of less than 2.0%. In other embodiments, the granules exhibit a friability of less than 1.5%. In other embodiments, the granules exhibit a friability of less than 1.0%. In yet other embodiments, the granules exhibit a friability of less than 0.5%.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein less than 30% of the cholestyramine is released after 6 hours at pH of 5.5 as measured using the USP Dissolution Apparatus 2 (paddle) Ph. Eur. 2.9.3.

In some embodiments, less than 25% of the cholestyramine is released after 6 hours at pH of 5.5 as measured using the USP Dissolution Apparatus 2 (paddle) Ph. Eur. 2.9.3. In other embodiments, less than 20% of the cholestyramine is released after 6 hours at pH of 5.5 as measured using the USP Dissolution Apparatus 2 (paddle) Ph. Eur. 2.9.3. In other embodiments, less than 15% of the cholestyramine is released after 6 hours at pH of 5.5 as measured using the USP Dissolution Apparatus 2 (paddle) Ph. Eur. 2.9.3. In yet other embodiments, less than 10% of the cholestyramine is released after 6 hours at pH of 5.5 as measured using the USP Dissolution Apparatus 2 (paddle) Ph. Eur. 2.9.3.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein the formulation exhibits less than 30% sequestration of cholic acid after 6 hours at pH 5.5 as measured using a USP Dissolution Apparatus 2 (paddle) Ph. Eur. 2.9.3.

In some embodiments, the formulation exhibits less than 25% sequestration of cholic acid after 6 hours at pH 5.5 as measured using a USP Dissolution Apparatus 2 (paddle) Ph. Eur. 2.9.3. In other embodiments, the formulation exhibits less than 20% sequestration of cholic acid after 6 hours at pH 5.5 as measured using a USP Dissolution Apparatus 2 (paddle) Ph. Eur. 2.9.3. In yet other embodiments, the formulation exhibits less than 15% sequestration of cholic acid after 6 hours at pH 5.5 as measured using a USP Dissolution Apparatus 2 (paddle) Ph. Eur. 2.9.3.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein the formulation exhibits greater than 30% sequestration of cholic acid after 2 hours at pH 1 followed by 4 hours at pH 6.8 as measured using a USP Dissolution Apparatus 2 (paddle) Ph. Eur. 2.9.3.

In some embodiments, the formulation exhibits greater than 35% sequestration of cholic acid after 2 hours at pH 1 followed by 4 hours at pH 6.8 as measured using a USP Dissolution Apparatus 2 (paddle) Ph. Eur. 2.9.3. In other embodiments, the formulation exhibits greater than 40% sequestration of cholic acid after 2 hours at pH 1 followed by 4 hours at pH 6.8 as measured using a USP Dissolution Apparatus 2 (paddle) Ph. Eur. 2.9.3. In yet other embodiments, the formulation exhibits greater than 45% sequestration of cholic acid after 2 hours at pH 1 followed by 4 hours at pH 6.8 as measured using a USP Dissolution Apparatus 2 (paddle) Ph. Eur. 2.9.3. In yet other embodiments, the formulation exhibits greater than 50% sequestration of cholic acid after 2 hours at pH 1 followed by 4 hours at pH 6.8 as measured using a USP Dissolution Apparatus 2 (paddle) Ph. Eur. 2.9.3.

In another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein the formulation exhibits less than 30% sequestration of cholic acid after 2 hours at pH 1 as measured using a USP Dissolution Apparatus 2 (paddle) Ph. Eur. 2.9.3.

In some embodiments, the formulation exhibits less than 25% sequestration of cholic acid after 2 hours at pH 1 as measured using a USP Dissolution Apparatus 2 (paddle) Ph. Eur. 2.9.3. In other embodiments, the formulation exhibits less than 20% sequestration of cholic acid after 2 hours at pH 1 as measured using a USP Dissolution Apparatus 2 (paddle) Ph. Eur. 2.9.3. In other embodiments, the formulation exhibits less than 15% sequestration of cholic acid after 2 hours at pH 1 as measured using a USP Dissolution Apparatus 2 (paddle) Ph. Eur. 2.9.3. In yet other embodiments, the formulation exhibits less than 10% sequestration of cholic acid after 2 hours at pH 1 as measured using a USP Dissolution Apparatus 2 (paddle) Ph. Eur. 2.9.3.

In yet another aspect, the invention relates to an oral formulation, comprising:
  a) a plurality of granules, each granule comprising cholestyramine; and
  b) a coating surrounding said granules, wherein the coating is capable of targeting release of the cholestyramine in the colon,
wherein the formulation exhibits greater than 30% sequestration of cholic acid after 2 hours at pH 1 followed by 4 hours at pH 7.4 as measured using a USP Dissolution Apparatus 2 (paddle) Ph. Eur. 2.9.3.

In some embodiments, the formulation exhibits greater than 35% sequestration of cholic acid after 2 hours at pH 1 followed by 4 hours at pH 7.4 as measured using a USP Dissolution Apparatus 2 (paddle) Ph. Eur. 2.9.3. In other embodiments, the formulation exhibits greater than 40% sequestration of cholic acid after 2 hours at pH 1 followed by 4 hours at pH 7.4 as measured using a USP Dissolution Apparatus 2 (paddle) Ph. Eur. 2.9.3. In other embodiments, the formulation exhibits greater than 45% sequestration of cholic acid after 2 hours at pH 1 followed by 4 hours at pH 7.4 as measured using a USP Dissolution Apparatus 2 (paddle) Ph. Eur. 2.9.3. In yet other embodiments, the formulation exhibits greater than 50% sequestration of cholic acid after 2 hours at pH 1 followed by 4 hours at pH 7.4 as measured using a USP Dissolution Apparatus 2 (paddle) Ph. Eur. 2.9.3.

The colon release coating should also prevent the cholestyramine granules from bursting. When water that diffuses through the coating is absorbed by the cholestyramine, the increasing volume of the cholestyramine leads to swelling of the granules. The coating of the granules should for that reason be sufficiently elastic in order to withstand the swelling of the granules. By preventing the granules from bursting, the coating avoids premature release of the cholestyramine.

The colon release coating consists of one or more coating layers that delay the availability of the cholestyramine to the intestinal content until the granules have reached the desired part of the colon. Techniques based on changes in the bacterial environment (i.e., enzyme-controlled release) or pH (pH-controlled release), based on gradual erosion of the coating (time-controlled release) or based on diffusion through a permeable film (diffusion-controlled release), or a combination of two or more of the above techniques may be used for controlling the release position and the rate of release of the granules.

Enzyme-Controlled Release Coating

In one embodiment, the colon release coating around the granules allows for enzyme-controlled release of the cholestyramine in the colon. The coating layer then comprises a biodegradable polymer that is degraded by bacterial enzymes present in the colon, but that is not degraded by the human enzymes present in the gastrointestinal tract. The release of the cholestyramine from the granules is thus triggered by changes in the bacterial environment and substantially prevented until the coated granules reach the colon.

The biodegradable polymer may be an azo polymer or a polysaccharide. Examples of bacterially degradable polysaccharides include chitosan, pectin, guar gum, dextran, inulin, starch and amylose, as well as derivatives thereof (Sinha and Kumria, *Eur. J. Pharm. Sci.* 2003, vol. 18, p. 3-18). The colon release coating preferably comprises starch.

The structure of starch generally comprises 20-30% (w/w) amylose, which is less easily degraded by intestinal microbiota, and 70-80% (w/w) amylopectin, which is more easily degraded by intestinal microbiota. Thus, depending on the specific amounts of amylose and amylopectin present in the structure, different types of starch have different degradation profiles. Resistant starch has a high amylose content and generally escapes from digestion in the small intestine. Such starch is instead digested by bacteria in the colon. Depending on the natural source of the starch and how it has been treated, resistant starch can be categorized into four types (RS1 to RS4), each having different properties. Resistant starch type 2 (RS2), such as in high amylose maize starch (or high amylose corn starch) is less accessible to enzymes due to the conformation of the starch. The colon release coating around the cholestyramine granules preferably comprises resistant starch type 2 (RS2). When RS2 is cooked or heated, realignment of the amylose and amylopectin crystalline structures occurs in a process called retrogradation, leading to resistant starch type 3 (RS3).

In addition to the biodegradable polymer, the coating layer comprises one or more further organic polymers. Examples of suitable organic polymers include, but are not limited to, poly(methyl acrylate-co-methyl methacrylate-co-methacrylic acid) 7:3:1 (Eudragit® FS 30 D), poly(ethyl acrylate-co-methyl methacrylate-co-trimethylammonioethyl methacrylate chloride) 1:2:0.2 (Eudragit® RL 30 D), poly (ethyl acrylate-co-methyl methacrylate-co-trimethylammonioethyl methacrylate chloride) 1:2:0.1 (Eudragit® RS 30 D), poly(ethyl acrylate-co-methyl methacrylate) 2:1 (Eudragit® NE 30 D or Eudragit® NM 30 D) and poly(vinyl acetate) (e.g., Kollicoat® SR 30 D). Preferably, the organic polymer is poly(methyl acrylate-co-methyl methacrylate-co-methacrylic acid) 7:3:1 (Eudragit® FS 30 D).

pH- and Diffusion-Controlled Coating

In another embodiment, the colon release coating around the granules allows for pH- and diffusion-controlled release of the cholestyramine in the colon. The coating then comprises a diffusion-controlled inner coating layer around the granules and an enteric (pH-controlled) outer coating layer.

The diffusion-controlled inner coating layer provides a modified release of the cholestyramine, i.e. the cholestyramine is not made available at once but over an extended period of time. The coating comprises one or more polymers that are insoluble at any pH value, but that are permeable to water and small molecules dissolved therein. Examples of such polymers include, but are not limited to, poly(ethyl acrylate-co-methyl methacrylate-co-trimethylammonioethyl methacrylate chloride) 1:2:0.2 (Eudragit® RL 30 D), poly(ethyl acrylate-co-methyl methacrylate-co-trimethylammonioethyl methacrylate chloride) 1:2:0.1 (Eudragit® RS 30 D), poly(ethyl acrylate-co-methyl methacrylate) 2:1 (Eudragit® NE 30 D or Eudragit® NM 30 D) and polyvinyl acetate (Kollicoat® SR 30 D). The diffusion-controlled inner coating preferably comprises poly(ethyl acrylate-co-methyl methacrylate-co-trimethylammonioethyl methacrylate chloride) 1:2:0.2 (Eudragit® RL 30 D), poly (ethyl acrylate-co-methyl methacrylate-co-trimethylammonioethyl methacrylate chloride) 1:2:0.1 (Eudragit® RS 30 D) or a combination thereof, and most preferably poly(ethyl acrylate-co-methyl methacrylate-co-trimethylammonioethyl methacrylate chloride) 1:2:0.1.

The enteric coating layer comprises a pH-sensitive polymer that is stable and insoluble at the acidic pH values found in the stomach (pH ~1-3) but that breaks down rapidly or becomes soluble at less acidic pH values, such as the pH values found in the small intestine (pH ~6 to 7). Examples of such pH-sensitive polymers include, but are not limited to, cellulose acetate phthalate, cellulose acetate succinate, hydroxypropyl methylcellulose acetate succinate, hydroxypropyl methylcellulose phthalate, poly(methacrylic acid-co-methyl methacrylate) 1:1 (Eudragit® L 100), poly(methacrylic acid-co-methyl methacrylate) 1:2 (Eudragit® S 100), poly(methacrylic acid-co-ethyl acrylate) 1:1 (Eudragit® L 100-55), poly(methyl acrylate-co-methyl methacrylate-co-methacrylic acid) 7:3:1 (Eudragit® FS 30 D), polyvinyl acetate phthalate, shellac, sodium alginate, and zein, as well as mixtures thereof. The enteric coating preferably comprises a pH-sensitive polymer selected from the group consisting of poly(methacrylic acid-co-methyl methacrylate) 1:1, hydroxypropyl methylcellulose acetate succinate and poly(methacrylic acid-co-methyl methacrylate) 1:2. The enteric coating most preferably comprises hydroxypropyl methylcellulose acetate succinate.

When water is absorbed by the cholestyramine, the increasing volume of the cholestyramine leads to swelling of the granules. The enzyme-controlled coating layer or the diffusion-controlled inner coating layer should therefore be elastic (i.e., have high elongation at break). Because of the elasticity of the coating layers, the coating is able to withstand this swelling. Burst of the granules and premature release of the cholestyramine is thereby avoided. The elasticity of the coating may be the result of the elasticity of the organic polymer(s) itself, or may be induced by the addition of a plasticizer. Examples of suitable plasticizers include, but are not limited to, triethyl citrate, glyceryl triacetate, tributyl citrate, diethyl phthalate, acetyl tributyl citrate, dibutyl phthalate and dibutyl sebacate.

In order to improve the adherence of the coating layer onto the cholestyramine granules, or in order to minimize the interaction between the coating layer(s) and the cholestyramine in the granules, an additional barrier coating layer may optionally be present between the granule and the coating layer. A barrier coating layer may also be present when two different coating layers should be kept physically separated from each other. A particularly suitable material for the barrier coating layer is hydroxypropyl methylcellulose (HPMC).

The controlled release coating layer(s) and the optional barrier coating layer(s) may comprise one or more additives, such as acids and bases, plasticizers, glidants, and surfactants. Examples of suitable acids include organic acids such as citric acid, acetic acid, trifluoroacetic acid, propionic acid, succinic acid, glycolic acid, lactic acid, malic acid, tartaric acid, ascorbic acid, pamoic acid, maleic acid, hydroxymaleic acid, phenylacetic acid, glutamic acid, benzoic acid, salicylic acid, mesylic acid, esylic acid, besylic acid, sulfanilic acid, 2-acetoxybenzoic acid, fumaric acid, toluenesulfonic acid, methanesulfonic acid, ethane disulfonic acid and oxalic acid, and inorganic acids such as hydrochloric acid, hydrobromic acid, sulphuric acid, sulfamic acid, phosphoric acid and nitric acid. Examples of suitable bases include inorganic bases such as sodium bicarbonate, sodium hydroxide and ammonium hydroxide. Examples of suitable plasticizers include triethyl citrate, glyceryl triacetate, tributyl citrate, diethyl phthalate, acetyl tributyl citrate, dibutyl phthalate and dibutyl sebacate Examples of suitable glidants include talc, glyceryl monostearate, oleic acid, medium chain triglycerides and colloidal silicon dioxide. Examples of suitable surfactants include sodium dodecyl sulfate, polysorbate 80 and sorbitan monooleate.

A thin layer of a non-sticking agent may ultimately be applied to the coated granules. This outer layer prevents the coated granules from sticking together, e.g. during storage. Examples of suitable non-sticking agents include fumed silica, talc and magnesium stearate.

The coating layers may be applied onto the cholestyramine granules by methods known in the art, such as by film coating involving perforated pans and fluidized beds.

The colon release coating substantially prevents release of the cholestyramine from the granules until they have reached the large intestine. Preferably, there should be no exposure of the cholestyramine in the small intestine, whereas the exposure should be quick once the multiparticulates have passed the ileocecal valve. In one embodiment, less than 30% of the cholestyramine is released in the small intestine, such as less than 20%, such as less than 10%. In a more preferred embodiment, less than 5% of the cholestyramine is released in the small intestine. In another embodiment, more than 70% of the cholestyramine is released in the colon, such as more than 80%, such as more than 90%. In a more preferred embodiment, more than 95% of the cholestyramine is released in the colon.

The colon release coating adds further weight and volume to the granules. The smaller the size of the granules, the larger is the impact of the coating on the volume of the final formulation. However, for reasons of patient compliance, it is desirable that the total volume of the formulation is kept as low as possible. The coating layer(s) should therefore be as thin as possible. Preferably, the amount of coating in the final formulation (on dry weight basis) is less than 50% w/w, more preferably less than 45% w/w, more preferably less than 40% w/w and even more preferably less than 35% w/w.

The cholestyramine content of the granules should be as high as possible. The uncoated granules therefore preferably contain at least 75% w/w cholestyramine, more preferably at least 80% w/w cholestyramine, even more preferably at least 85% w/w cholestyramine and most preferably at least 90% w/w cholestyramine. The cholestyramine content of the final formulation (on dry weight basis) is preferably at least 50% w/w, and more preferably at least 55% w/w.

The oral formulation described herein may be administered to a patient in different forms, depending on factors such as the age and general physical condition of the patient. For example, the formulation may be administered in the form of one or more capsules wherein the coated granules are contained. Such capsules conventionally comprise a degradable material, such as gelatin, hydroxypropyl methylcellulose (HPMC), pullulan or starch, which easily disintegrates under the acidic conditions in the stomach. The coated granules are thereby quickly released into the stomach. Thus, in one aspect, the invention relates to a capsule comprising the oral formulation disclosed herein.

Alternatively, the coated granules may be administered as a sprinkle formulation, the contents of which can be dispersed in liquid or soft food. Such a formulation does not require the swallowing of larger capsules and is therefore particularly useful for infants and small children as well as for older adults. Thus, in another aspect, the invention relates to a sprinkle formulation comprising the oral formulation disclosed herein. In such a formulation, the coated granules may be contained within a capsule, sachet or stick pack.

The oral formulation disclosed herein provides several advantages over other formulations. The small coated granules (multiparticulates) according to the present invention are able to easily pass the gastrointestinal tract. This eliminates the risk that the formulation is temporarily held up in the gastrointestinal tract, such as at the stomach or at the ileocecal valve, as is sometimes encountered with monolithic formulations (such as tablets or capsules that do not disintegrate in the stomach). Furthermore, the cholestyramine is made available to the intestinal content only when the colon release coating starts being degraded in the lower gastrointestinal tract, in particular the colon. The contents of the stomach and the small intestine are therefore effectively protected from the cholestyramine, which is a major improvement over formulations that directly release the cholestyramine in the stomach or the small intestine. Because the cholestyramine is made available to the intestinal content only after reaching the colon, the oral formulation disclosed herein also reduces undesired interactions of cholestyramine with other components in the gastrointestinal tract, such as other drugs or nutrients.

The low solubility of cholestyramine in aqueous environment prevents the release of cholestyramine from the formulation to be measured directly. The availability of the cholestyramine to the intestinal content over time and at different pH values can instead be determined in vitro, such as by measuring the sequestering capacity of the formulation under simulated conditions for the gastrointestinal tract. Such a method involves measuring the decreasing amount of free bile acid (i.e., the compound to be sequestered) in a liquid medium representative of the gastrointestinal tract, as described in the experimental section. See also the Official Monograph for cholestyramine resin (USP 40, page 3404).

For instance, the sequestering capacities of the cholestyramine formulations may be studied using the Simulator of the Human Intestinal Microbial Ecosystem (SHIME®) as developed by ProDigest (Ghent, Belgium). As described in more detail in the experimental section, this model enables the in vitro evaluation of the bile acid binding capacity of cholestyramine formulations under physiological conditions representative for fasted stomach, small intestine and proximal colon. Bile acids such as cholic acid (CA), chenodeoxycholic acid (CDCA) and deoxycholic acid (DCA) may be used in such studies, or a mixture of two or more of these bile salts. A 40:40:20 (w/w) mixture of CA, CDCA and DCA is preferably used as a representative mixture of human bile salts. Experiments on cholestyramine formulations should be run in parallel with a control experiment to which no cholestyramine is added, in order to monitor the degradation of the bile salts under the conditions used in the assay. For each experiment, samples are taken at selected time intervals and the concentrations of the bile acids in the samples are determined, e.g. by means of HPLC. From these data, the percentage of remaining bile acids in each studied sample may be calculated as the ratio of the value of the studied sample to the value of the control sample at the corresponding incubation time:

$$\% \text{ remaining bile acid} = \frac{\text{concentration of } BA \text{ in sample}}{\text{concentration of } BA \text{ in control sample}} \times 100$$

A plot of the percentage of remaining bile acids against time will show the decrease of bile acids, i.e. the sequestration of bile acids by the cholestyramine formulations, during small intestinal and colonic incubation.

In another aspect, the invention relates to an oral formulation, comprising:
 a) a plurality of granules, each granule comprising cholestyramine; and
 b) a coating surrounding each granule, wherein the coating is capable of targeting release of the cholestyramine in the colon;
wherein the oral formulation herein exhibits less than about 30% sequestration of one or more of cholic acid, chenodeoxycholic acid, and deoxycholic acid after 2 hours in small intestinal incubations as measured in the Simulator of the Human Intestinal Microbial Ecosystem (SHIME) model.

In some embodiments, the oral formulation exhibits less than about 25% sequestration of one or more of cholic acid, chenodeoxycholic acid, and deoxycholic acid after 2 hours in small intestinal incubations as measured in the Simulator of the Human Intestinal Microbial Ecosystem (SHIME) model. In other embodiments, the oral formulation exhibits less than about 20% sequestration of one or more of cholic acid, chenodeoxycholic acid, and deoxycholic acid after 2 hours in small intestinal incubations as measured in the Simulator of the Human Intestinal Microbial Ecosystem (SHIME) model. In yet other embodiments, the oral formulation exhibits less than about 15% sequestration of one or more of cholic acid, chenodeoxycholic acid, and deoxycholic acid after 2 hours in small intestinal incubations as measured in the Simulator of the Human Intestinal Microbial Ecosystem (SHIME) model.

In another aspect, the invention relates to the formulation disclosed herein for use in the treatment or prevention of bile acid malabsorption.

The invention also relates to the use of the formulation disclosed herein in the manufacture of a medicament for the treatment or prevention of bile acid malabsorption. The invention further relates to a method for the treatment or prevention of bile acid malabsorption comprising administering to a mammal in need of such treatment or prevention a therapeutically effective amount of the formulation disclosed herein.

Bile acid malabsorption may be divided into three different types, dependent on the cause of the failure of the distal ileum to absorb bile acids. Type 1 BAM is the result of (terminal) ileal disease (such as Crohn's disease) or (terminal) ileal resection or bypass. Type 2 BAM is often referred to as idiopathic bile acid malabsorption or primary bile acid diarrhoea (BAD) and is believed to be the result of an overproduction of bile acids or caused by a defective feedback inhibition of hepatic bile acid synthesis. This feedback regulation is mediated by the ileal hormone fibroblast growth factor 19 (FGF19) in man. Finally, type 3 BAM may be the result of cholecystectomy, vagotomy, small intestinal bacterial overgrowth (SIBO), coeliac disease, pancreatic insufficiency (chronic pancreatitis, cystic fibrosis), pancreatic transplant, radiation enteritis, collagenous colitis, microscopic colitis, lymphocytic colitis, ulcerative colitis or irritable bowel syndrome (i.e., diarrhoea-predominant irritable bowel syndrome (IBS-D)).

The formulation may also be used in combination with an Ileal Bile Acid Absorption (IBAT) inhibitor. Treatment with IBAT inhibitors, such as in the treatment of liver diseases, disorders of fatty acid metabolism or glucose utilization disorders, may result in increased levels of bile acids and/or influence the reabsorption of bile acids by the small intestine, leading to high concentrations of bile acid in the large intestine and thus causing diarrhoea. This side effect of the treatment with IBAT inhibitors may be treated or prevented by treatment with the formulation as disclosed herein. The formulation and the IBAT inhibitor may be administered simultaneously, sequentially or separately.

Thus, in another aspect, the invention relates to the formulation disclosed herein, for use in the treatment or prevention of diarrhoea upon oral administration of an IBAT inhibitor.

The invention also relates to the use of the formulation disclosed herein in the manufacture of a medicament for the treatment or prevention of diarrhoea upon oral administration of an IBAT inhibitor. The invention further relates to a method for the treatment or prevention of diarrhoea upon oral administration of an IBAT inhibitor, comprising administering to a mammal in need of such treatment or prevention therapeutically effective amounts of an IBAT inhibitor and of the formulation disclosed herein.

In a preferred embodiment, the invention relates to the formulation disclosed herein, for use in the treatment or prevention of bile acid diarrhoea upon treatment of a liver disease, such as a cholestatic liver disease, comprising oral administration of an IBAT inhibitor. In particular, the invention relates to the formulation disclosed herein for use in the treatment or prevention of diarrhoea upon treatment of Alagilles syndrome (ALGS), progressive familial intrahepatic cholestasis (PFIC), primary biliary cirrhosis (PBC), primary sclerosing cholangitis (PSC), autoimmune hepatitis, cholestatic pruritus, non-alcoholic fatty liver disease (NAFLD) or non-alcoholic steatohepatitis (NASH) comprising oral administration of an IBAT inhibitor.

In another embodiment, the invention relates to a method for the treatment or prevention of bile acid diarrhoea upon treatment of a liver disease comprising oral administration of an IBAT inhibitor, comprising administering to a mammal in need of such treatment or prevention a therapeutically effective amount of the formulation disclosed herein. In particular, the invention relates to such a method for the treatment or prevention of diarrhoea wherein the liver disease is Alagilles syndrome (ALGS), progressive familial intrahepatic cholestasis (PFIC), primary biliary cirrhosis (PBC), primary sclerosing cholangitis (PSC), autoimmune hepatitis, cholestatic pruritus, non-alcoholic fatty liver disease (NAFLD) or non-alcoholic steatohepatitis (NASH).

A liver disease as defined herein is any bile acid-dependent disease in the liver and in organs connected therewith, such as the pancreas, portal vein, the liver parenchyma, the intrahepatic biliary tree, the extrahepatic biliary tree, and the gall bladder. Liver diseases include, but are not limited to an inherited metabolic disorder of the liver; inborn errors of bile acid synthesis; congenital bile duct anomalies; biliary atresia; neonatal hepatitis; neonatal cholestasis; hereditary forms of cholestasis; cerebrotendinous xanthomatosis; a secondary defect of BA synthesis; Zellweger's syndrome; cystic fibrosis (manifestations in the liver); alpha1-antitrypsin deficiency; Alagilles syndrome (ALGS); Byler syndrome; a primary defect of bile acid (BA) synthesis; progressive familial intrahepatic cholestasis (PFIC) including PFIC-1, PFIC-2, PFIC-3 and non-specified PFIC; benign recurrent intrahepatic cholestasis (BRIC) including BRIC1, BRIC2 and non-specified BRIC; autoimmune hepatitis; primary biliary cirrhosis (PBC); liver fibrosis; non-alcoholic fatty liver disease (NAFLD); non-alcoholic steatohepatitis (NASH); portal hypertension; general cholestasis; jaundice during pregnancy; jaundice due to drugs; intrahepatic cholestasis; extrahepatic cholestasis; primary sclerosing cholangitis (PSC); gall stones and choledocholithiasis; malignancy causing obstruction of the biliary tree; pruritus due to cholestasis or jaundice; pancreatitis; chronic autoimmune liver disease leading to progressive cholestasis; hepatic steatosis; alcoholic hepatitis; acute fatty liver; fatty liver of pregnancy; drug-induced hepatitis; iron overload disorders; hepatic fibrosis; hepatic cirrhosis; amyloidosis; viral hepatitis; and problems in relation to cholestasis due to tumours and neoplasms of the liver, of the biliary tract and of the pancreas.

Disorders of fatty acid metabolism and glucose utilization disorders include, but are not limited to, hypercholesterolemia, dyslipidemia, metabolic syndrome, obesity, disorders of fatty acid metabolism, glucose utilization disorders, disorders in which insulin resistance is involved, and type 1 and type 2 diabetes mellitus.

IBAT inhibitors are often referred to by different names. As used herein, the term "IBAT inhibitors" should be understood as also encompassing compounds known in the literature as Apical Sodium-dependent Bile Acid Transporter Inhibitors (ASBTI's), bile acid transporter (BAT) inhibitors, ileal sodium/bile acid cotransporter system inhibitors, apical sodium-bile acid cotransporter inhibitors, ileal sodium-dependent bile acid transport inhibitors, bile acid reabsorption inhibitors (BARI's), and sodium bile acid transporter (SBAT) inhibitors.

IBAT inhibitors that can be used in combination with the bile acid sequestrant formulation disclosed herein include, but are not limited to, benzothiazepines, benzothiepines, 1,4-benzothiazepines, 1,5-benzothiazepines and 1,2,5-benzothiadiazepines.

Suitable examples of IBAT inhibitors that can be used in combination with the bile acid sequestrant formulation disclosed herein include, but are not limited to, the compounds disclosed in WO 93/16055, WO 94/18183, WO 94/18184, WO 96/05188, WO 96/08484, WO 96/16051, WO 97/33882, WO 98/03818, WO 98/07449, WO 98/40375, WO 99/35135, WO 99/64409, WO 99/64410, WO 00/47568, WO00/61568, WO 00/38725, WO 00/38726, WO 00/38727, WO 00/38728, WO 00/38729, WO 01/68096, WO 02/32428, WO 03/061663, WO 2004/006899, WO 2007/009655, WO 2007/009656, DE 19825804, EP 864582, EP 489423, EP 549967, EP 573848, EP 624593, EP 624594, EP 624595, EP 624596, EP 0864582, EP 1173205 and EP 1535913.

Particularly suitable IBAT inhibitors are those disclosed in WO 01/66533, WO 02/50051, WO 03/022286, WO 03/020710, WO 03/022825, WO 03/022830, WO 03/091232, WO 03/106482 and WO 2004/076430, and especially the compounds selected from the group consisting of:

1,1-dioxo-3,3-dibutyl-5-phenyl-7-methylthio-8-(N-{(R)-α-[N-(carboxymethyl)carbamoyl]-benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N'—((S)-1-carboxyethyl)carbamoyl]-benzyl}carbamoylmethoxy)-2,3,4,5-tetra hydro-1,5-benzothiazepine;

1,1-dioxo-3,3-dibutyl-5-phenyl-7-methylthio-8-(N-{(R)-α-[N—((S)-1-carboxypropyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((R)-1-carboxy-2-methylthioethyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-methylpropyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N—((S)-1-carboxyethyl)carbamoyl]-benzyl}carbamoylmethoxy)-2,3,4,5-tetrahydro-1,2,5-benzothiadiazepine;

1, 1-dioxo-3, 3-dibutyl-5-phenyl-7-methylthio-8-(N-{(R)-α-[N'—((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N—((S)-1-carboxyethyl)carbamoyl]-4-hydroxybenzyl}carbamoylmethoxy)-2,3,4,5-tetra hydro-1,2,5-benzothiadiazepine;

1,1-dioxo-3,3-dibutyl-5-phenyl-7-methylthio-8-(N-{(R)-α-[N—((S)-1-carboxy-2-methylpropyl)-carbamoyl]-4-hydroxybenzyl}carbamoylmethoxy)-2,3,4,5-tetra hydro-1,2,5-benzothiadiazepine; and 1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

or a pharmaceutically acceptable salt thereof.

Other particularly suitable IBAT inhibitors are those disclosed in WO99/32478, WO00/01687, WO01/68637, WO03/022804, WO 2008/058628 and WO 2008/058630, and especially the compounds selected from the group consisting of:

1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate;

1-[[4-[[4-[3,3-dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniazabicyclo[2.2.2]octane chloride;

1-[[5-[[3-[(3S,4R,5R)-3-butyl-7-(dimethylamino)-3-ethyl-2,3,4,5-tetra hydro-4-hydroxy-1,1-dioxido-1-benzothiepin-5-yl]phenyl]amino]-5-oxopentyl]amino]-1-deoxy-D-glucitol; and potassium ((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetra hydro-1H-benzo[b]thiepin-5-yl)-phenyl]-ureido}-3,5-dihydroxy-tetrahydro-pyran-2-ylmethyl)sulphate, ethanolate, hydrate.

An effective amount of the cholestyramine formulation according to the invention can be any amount containing more than or equal to about 100 mg of cholestyramine, such as more than or equal to about 250 mg, 500 mg, 750 mg, 1000 mg, 1250 mg, 1500 mg, 1750 mg or 2000 mg of cholestyramine. For example, the effective amount of cholestyramine can be between 100 mg and 5000 mg, such as between 250 mg and 2500 mg, between 250 mg and 2000 mg, between 500 mg and 2500 mg, between 500 mg and 2000 mg, or between 750 mg and 2000 mg.

A unit dose of the cholestyramine formulation according to the invention may comprise from 200 to 300 mg of cholestyramine, such as from 220 to 280 mg of cholestyramine, such as from 240 to 260 mg of cholestyramine. A unit dose preferably comprises about 250 mg of cholestyramine. The daily dose can be administered as a single dose or divided into one, two, three or more unit doses.

The frequency of administration of the formulation as disclosed herein can be any frequency that reduces the bile acid malabsorption condition without causing any significant adverse effects or toxicity to the patient. The frequency of administration can vary from once or twice a week to several times a day, such as once a day or twice a day. The frequency of administration can furthermore remain constant or be variable during the duration of the treatment.

Several factors can influence the frequency of administration and the effective amount of the formulation that should be used for a particular application, such as the severity of the condition being treated, the duration of the treatment, as well as the age, weight, sex, diet and general medical condition of the patient being treated.

The invention is further illustrated by means of the following examples, which do not limit the invention in any respect. All cited documents and references are incorporated herein by reference.

EXAMPLES

Example 1

Preparation of Granules

All experiments were performed on a 200 g scale. The dry ingredients (cholestyramine and copovidone; see amounts in table 1 below) were mixed in a Kenwood Patissier for 1 minute. When Eudragit® RL 30 D (a 30% aqueous dispersion) was included in the experiment, the appropriate amount of the dispersion was diluted with water up to a total weight of about 300 gram. Water, or the dilute Eudragit dispersion, was then added to the dry ingredients in three portions of about 100 gram with 3 minutes of mixing after each addition. A further portion of pure water (between 60 and 100 g) was thereafter added, so that the total amount of added water equalled about 2.1 times the amount of cholestyramine (w/w). After mixing was continued for 1 minute, the wet mass was transferred to a stainless steel tray and dried in a drying oven at 50° C. overnight.

The dried material was milled in a Quadro Comil U5, equipped with a 4 mm screen and operating at 1000 rpm (revolutions per minute). The granules were sieved and the fraction between 1.0 and 1.6 mm was collected. The fraction that was larger than 1.6 mm was returned to the mill and milled once more.

Friability testing was performed using the equipment and procedure described in European Pharmacopoeia 8.0, test 2.9.41. The granules were sieved on a 500 μm sieve to remove any loose dust before weighing. The results are shown in table 1 below.

TABLE 1

| Entry | Amount (% w/w) | | | | Yield (%) | Friability (%) |
| | Cholestyr-amine | Copovidone | MCC | Eudragit ® RL 30 D* | | |
| --- | --- | --- | --- | --- | --- | --- |
| 1 | 85 | 7.5 | 4.5 | 3 | 45 | 1.5 |
| 2 | 93 | 7 | 0 | 0 | 43 | 2.0 |
| 3 | 92 | 6 | 0 | 2 | 46 | 1.7 |
| 4 | 92 | 5 | 0 | 3 | 46 | 0.8 |
| 5** | 83 | 6 | 10 | 1 | 49 | 3.1 |

*The amount refers to dry polymer weight
**The total amount of water was about 2.4 times the amount of cholestyramine (w/w)

Coating experiments (such as those in Examples 3 and 4 below) confirmed that the obtained granules were sufficiently stable for being coated with one or more coating layers.

Example 2

Disintegration Testing of Cholestyramine Granules

Granules from example 1 (10 g) are added to 400 mL of a phosphate buffer (50 mM, pH 6.8) under stirring at 300 rpm using a propeller stirrer. The time for the granules to fully disintegrate is measured.

Example 3

Formulations A-C for Enzyme-Controlled Release

The cholestyramine granules of Example 1, entry 1 were formulated with a colon release coating based on Eudragit® FS 30 D and native high amylose maize starch.

The granules composition for a unit dose comprising 250 mg cholestyramine is shown below.

| Ingredient | Amount (mg/dose) |
| --- | --- |
| Cholestyramine | 250 |
| Copovidone (Kollidon ® VA64 Fine) | 22.1 |
| Microcrystalline cellulose (Avicel ® PH102) | 13.2 |
| Poly(ethyl acrylate-co-methyl methacrylate-co-trimethylammonioethyl methacrylate chloride) 1:2:0.2 (Eudragit ® RL 30 D) | 8.8 |
| Total | 294.1 |

For the coating, a glycerol monostearate (GMS) emulsion containing GMS, polysorbate 80 and triethyl citrate was prepared according to general instructions from Evonik. The emulsion was then mixed with Eudragit® FS 30 D (aqueous dispersion 30%). The composition of the Eudragit FS 30 D coating dispersion, based on dry weight, is shown below. The concentration, based on dry weight, is 19.8% (w/w).

| Ingredient | Amount (w/w) |
| --- | --- |
| Poly(methyl acrylate-co-methyl methacrylate-co-methacrylic acid) 7:3:1 (Eudragit ® FS 30 D) | 90.4 |
| Triethyl citrate | 4.5 |
| Glycerol monostearate 45-55 (Kolliwax ® GMS II) | 3.6 |
| Polysorbate 80 (Tween ® 80) | 1.5 |

The pH of the dispersion was adjusted with a 0.3 M NaOH solution to 5.5. The dispersion was mixed with a suspension of native starch granules containing 12.9% starch, 0.1% Kolliphor® SLS fine and water. The Eudragit® dispersion was mixed with the starch suspension so that the ratio between polymer film and starch in the final film is 60% starch to 40% Eudragit® FS 30 D film. The composition of the coating, based on dry weight, is shown below. The concentration, based on dry weight of the applied dispersion, is 15% (w/w).

| Ingredient | Amount (w/w) |
| --- | --- |
| Poly(methyl acrylate-co-methyl methacrylate-co-methacrylic acid) 7:3:1 (Eudragit ® FS 30 D) | 36.0 |
| High amylose maize starch (Hylon ® VII) | 59.7 |
| Triethyl citrate | 1.8 |
| Glycerol monostearate 45-55 (Kolliwax ® GMS II) | 1.4 |
| Polysorbate 80 (Tween ® 80) | 0.6 |
| Sodium lauryl sulphate (Kolliphor ® SLS Fine) | 0.5 |
| NaOH | qs pH 5.5 |

The coating layer was applied using a Huttlin Kugelcoater HKC005. The initial batch size was 65 g. The coating process was performed with an air inlet temperature of 47-52° C., resulting in a product temperature of 27-29° C. The air flow was adjusted to achieve an appropriate fluidization of the granules during the coating.

The coating was applied to the cholestyramine granules so as to obtain a weight gain of ~50% (formulation A), ~75% (formulation B) or ~100% (formulation C). After the coating, the granules were heat-treated at 40° C. for 2 hours.

The coated granules may be encapsulated in capsules, e.g. hard gelatine capsules. Details for the final formulations (on dry weight basis) are shown below:

|  | Formulation A | Formulation B | Formulation C |
|---|---|---|---|
| Dose weight: | 441 mg | 515 mg | 588 mg |
| Cholestyramine: | 250 mg (57%) | 250 mg (49%) | 250 mg (43%) |
| Coating: | 147 mg (33%) | 221 (43%) | 294 mg (50%) |

Example 4

Formulations D-F for pH- and Diffusion-Controlled Release

The cholestyramine granules of Example 1 are formulated with a colon release coating comprising an diffusion controlled inner coating based on poly(ethyl acrylate-co-methyl methacrylate-co-trimethylammonioethyl methacrylate chloride) and an enteric outer coating based on hydroxypropyl methylcellulose acetate succinate.

Three formulations are prepared with different amounts of poly(ethyl acrylate-co-methyl methacrylate-co-trimethylammonioethyl methacrylate chloride) in the inner coating, as follows:

Formulation D: 100% Eudragit® RL 30 D
Formulation E: 50% Eudragit® RL 30 D+50% Eudragit® RS 30 D
Formulation F: 100% Eudragit® RS 30 D The granules composition for a unit dose comprising 250 mg cholestyramine is shown below.

| Ingredient | Amount (mg/dose) |
|---|---|
| Cholestyramine | 250 |
| Copovidone (Kollidon ® VA64 Fine) | 22.1 |
| Microcrystalline cellulose (Avicel ® PH102) | 13.2 |
| Poly(ethyl acrylate-co-methyl methacrylate-co-trimethylammonioethyl methacrylate chloride) 1:2:0.2 (Eudragit ® RL 30 D) | 8.8 |
| Total | 294.1 |

Inner Coating

A glycerol monostearate (GMS) emulsion containing GMS, polysorbate 80 and triethyl citrate is prepared according to general instructions from Evonik. The emulsion is mixed with Eudragit RL30D/RS30D dispersion (30% w/w). The composition of the inner coating film, based on dry weight, is shown below. The concentration, based on dry weight of the applied dispersion, is 19.8% (w/w).

| Ingredient Inner coating | Amount (w/w) |
|---|---|
| Poly(ethyl acrylate-co-methyl methacrylate-co-trimethylammonioethyl methacrylate chloride) 1:2:0.2 (Eudragit ® RL 30 D) or 1:2:0.1 (Eudragit ® RS 30 D) | 90.4 |
| Triethyl citrate | 4.5 |
| Glycerol monostearate 45-55 (Kolliwax ® GMS II) | 3.6 |
| Polysorbate 80 (Tween ® 80) | 1.5 |

The coating layer is applied using a Huttlin Kugelcoater HKC005; batch size 75 g. The coating process is performed with an air inlet temperature of 45° C., resulting in a product temperature of 27-29° C. Air flow is adjusted to achieve an appropriate fluidization of the granules during the coating. The coating is applied to the granules so as to obtain a weight gain of 10%. After the coating, the granules are heat-treated at 40° C. for 24 hours.

Outer Coating

The enteric coating is prepared by mixing 7% w/w hypromellose acetate succinate, 2.45% w/w triethyl citrate, 2.1% w/w talc, 0.21% w/w sodium lauryl sulphate and 88.24% w/w water for 30 min with an overhead stirrer at low temperature, <15° C. The composition of the outer coating film, based on dry weight, is shown below. The coating liquid is kept below 15° C. during the coating process.

| Ingredient Outer coating | Amount (w/w) |
|---|---|
| Hypromellose acetate succinate (AQOAT AS HF) | 59.5 |
| Triethyl citrate | 20.8 |
| Talc, micronized | 17.9 |
| Sodium lauryl sulphate (Kolliphor ® SLS Fine) | 1.8 |

The coating layer is applied using a Huttlin Kugelcoater HKC005; batch size 75 g. The coating process is performed with an air inlet temperature of 55° C., resulting in a product temperature of 32° C. Air flow is adjusted to achieve an appropriate fluidization of the granules during the coating. The enteric coating is applied to the granules so as to obtain a weight gain of 40% (based on the weight of the coated granules after application of the inner coating). After the coating, the granules are heat-treated at 40° C./75% RH for 48 hours.

The coated granules may be encapsulated in capsules, e.g. hard gelatine capsules. Details for the final formulations (on dry weight basis) are shown below:

| Dose weight: | 452.9 mg |
|---|---|
| Cholestyramine: | 250 mg (55%) |
| Inner coating: | 29.4 mg |
| Outer coating: | 129.4 mg |
| Total coating: | 158.8 mg (35%) |

Example 5

Sequestration Assay

The sequestering capacities of formulations A, B and C was determined in a simplified assay, simulating the pH of the stomach and the small intestine. The sequestration was determined by measuring the decreasing amount of cholic acid in an aqueous solution. The USP Dissolution Apparatus 2 (paddle) Ph. Eur. 2.9.3 was used.

Sequestration at pH 5.5

An amount of a formulation A, B or C corresponding to 250 mg cholestyramine was added to a vessel containing 500 mL of a buffered solution of cholic acid (0.192 mg/mL), pH 5.5 and the contents were stirred at 75 rpm for 6 hours. Samples of the solution were withdrawn at different time points and analysed for cholic acid by HPLC using a Thermo Hypersil Gold column, 50 mm×2.1 mm, particle size 1.9 μm; column temperature 60° C.; mobile phase 30:70 acetonitrile:phosphate buffer (pH 3.0); flow rate 0.75 mL/min. 3 replicate samples were analysed for each formulation and the average values were calculated.

Sequestration at pH 6.8

An amount of a formulation A, B, or C corresponding to 250 mg cholestyramine was added to a vessel containing 250 mL 0.1 M hydrochloric acid solution (pH 1) and the contents were stirred at 75 rpm for 2 hours. 250 mL of a solution of cholic acid in potassium hydroxide/potassium phosphate buffer solution was then added to the vessel, giving a buffered solution of cholic acid (0.192 mg/mL) with pH 6.8. After 1 minute of mixing, a first sample was removed. The pH was thereafter verified and if necessary adjusted to 6.8 by addition of the appropriate amount of 0.1 M potassium hydroxide solution. The solution was thereafter mixed for an additional 6 hours. Samples of the solution were withdrawn at different time points and analysed for cholic acid by HPLC using a Thermo Hypersil Gold column, 50 mm×2.1 mm, particle size 1.9 µm; column temperature 60° C.; mobile phase 30:70 acetonitrile:phosphate buffer (pH 3.0); flow rate 0.75 mL/min. 3 replicate samples were analysed for each formulation and the average values were calculated.

Figure 1B:
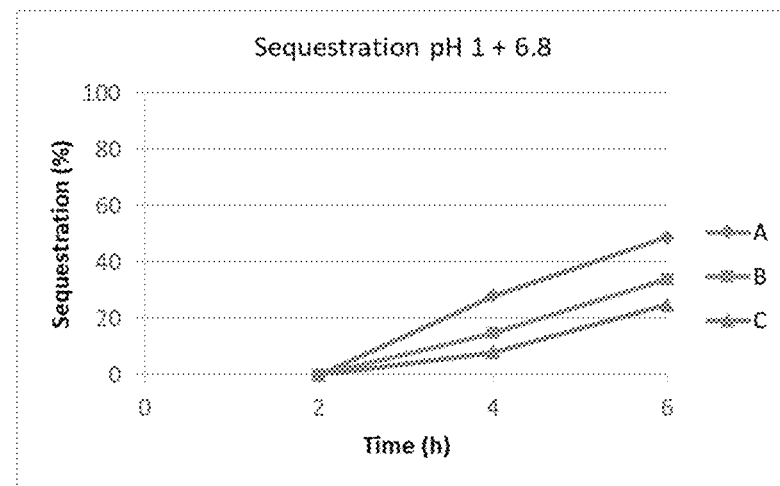

The sequestration profiles for formulations A-C are shown in FIG. 1. The pH of 5.5 is slightly lower than the pH normally observed in the duodenum, although it may occur in some patients and healthy persons. At this pH, sequestration is limited for all formulations (FIG. 1A). Sequestration at pH 6.8 is representative for the conditions in the ileum. At this pH, formulation A gave 49% sequestration after 4 hours, formulation B gave 34% sequestration and formulation C gave 25% sequestration (FIG. 1B).

Example 6

In Vitro Determination of the Sequestering Capacity of Cholestyramine Formulations Under Simulated Conditions for the Gastrointestinal Tract The sequestering capacities of the cholestyramine formulations are studied in the Simulator of the Human Intestinal Microbial Ecosystem (SHIME®) as developed by ProDigest (Ghent, Belgium). The simulator is adapted to evaluate the sequestering capacity of binding bile salts under physiological conditions representative for fasted stomach, small intestine and proximal colon. The liquid media representative of the fasted stomach and small intestine have previously been described by Marzorati et al. (*LWT-Food Sci. Technol.* 2015, vol. 60, p. 544-551). The liquid medium for the proximal colon comprises a SHIME® matrix containing a stable microbial community representative for the human colon. A method for obtaining a stable microbial community of the human intestine is described by Possemiers et al. (*FEMS Microbiol. Ecol.* 2004, vol. 49, p. 495-507) and references therein. The sequestration is determined by measuring the decreasing amount of bile acids in an aqueous solution. A 40:40:20 (w/w) mixture of cholic acid (CA), chenodeoxycholic acid (CDCA) and deoxycholic acid (DCA) is used as a representative mixture of human bile salts (Carulli et al., *Aliment. Pharmacol. Ther.* 2000, vol. 14, issue supplement s2, p. 14-18).

A comparative experiment to which pure (unformulated) cholestyramine powder is added is also conducted. A control experiment to which no cholestyramine is added is conducted in order to monitor the degradation of the bile salts under the colonic conditions used in the assay.

Each experiment is performed in triplicate to account for biological variation.

Fasted Stomach

Amounts of formulations A, B and C corresponding to 91 mg of cholestyramine and the pure cholestyramine (91 mg) are dosed to 14 mL fasted stomach liquid medium (pH 1.8). The digests are incubated for 1 hour at 37° C.

Small Intestine

After one hour of stomach incubation, 5.6 mL pancreatic juice (pH 6.8) containing the defined 40:40:20 mixture of bile salts (46.7 mM) is added. The small intestine digests are incubated for 2 hours at 37° C. and samples are taken after 0, 60 and 120 minutes.

Proximal Colon

After two hours of small intestine incubation, 42 mL of a full SHIME® matrix (pH 6.0) originated from the ascending colon of a SHIME® system is added. The colon digests are incubated for 24 hours at 37° C. and samples are collected every hour for the first 6 hours and then at 19 h and at 24 h.

Sample Analysis

The concentration of free bile salts in the samples is assessed by means of HPLC. A calibration curve is used to calculate the concentrations of CA, CDCA and DCA in the samples. One mL of each sample is centrifuged for 2 min at 5000 g. 500 µL of the supernatant is mixed with 500 µL of an 80:20 (v:v) mixture of methanol and phosphate buffer, vigorously vortexed, filtered through a 0.2 µm PTFE filter and injected in a Hitachi Chromaster HPLC equipped with a UV-Vis detector. The three bile salts are separated by a reversed-phase C18 column (Hydro-RP, 4 µm, 80 Å, 250× 4.6 mm, Synergi). The separation is performed under isocratic conditions at room temperature, using a 80:20 (v:v) mixture of methanol and phosphate buffer as the mobile phase. The analysis is performed at 0.7 mL/min during 23 minutes and the bile salts are detected at 210 nm. The injection volume is set at 20 µL for stomach and small intestine samples and 50 µL for colon samples.

The full SHIME® matrix that is used for the colonic incubations contains (degraded) bile salts originating from BD Difco™ Oxgall, a dehydrated fresh bile extract from bovine origin (Catalog Number 212820). Although the exact composition of this mixture is unknown, a higher quantity of free bile salts might be expected in the colon samples. The values of the background (i.e. blank sample where no mix of bile salts is added) are therefore subtracted from each sample in order to take into account the 'baseline' of free bile salts present in the total SHIME® matrix.

The measured concentrations of the different bile acids in the control sample will show the effect and extent of microbial salt metabolism in the gut (e.g. deconjugation, dehydrogenation and dehydroxylation), particularly in the colon. A sudden and large decrease of the concentrations of CA, CDCA and DCA in the control sample may be observed during the transition of the small intestinal to the colonic incubation.

The percentage of remaining bile acids in each studied sample may be calculated as the ratio of the value of the studied sample to the value of the control sample at the corresponding incubation time. A plot of the percentage of remaining bile acids against time will show the decrease of bile acids, i.e. the sequestration of bile acids by the cholestyramine formulations, during small intestinal and colonic incubation.

The invention claimed is:

1. A population of granules, each granule comprising a homogenous mixture of at least 70% w/w cholestyramine and
   i. a combination of at least 6% w/w of a binding agent and at least 2% w/w of an acrylate copolymer; or
   ii. a combination of at least 5% w/w of a binding agent and at least 3% w/w of an acrylate copolymer; or
   iii. a combination of at least 6% w/w of a binding agent, at least 1% w/w of an acrylate copolymer and from 5% to 15% w/w microcrystalline cellulose;
wherein the binding agent comprises a cellulose ether, a vinylpyrrolidone-based polymer, or a combination thereof.

2. The granules according to claim 1, wherein the binding agent is a cellulose ether.

3. The granules according to claim 1, wherein the binding agent is a vinylpyrrolidone-based polymer.

4. The granules according to claim 1, wherein the binding agent comprises a combination of a cellulose ether and a vinylpyrrolidone-based polymer.

5. The granules according to claim 1, wherein the cellulose ether is methyl cellulose, hydroxypropylcellulose, hydroxypropyl methylcellulose or sodium carboxymethyl cellulose, or a mixture comprising two or more of these cellulose ethers.

6. The granules according to claim 1, wherein the vinylpyrrolidone-based polymer is copovidone.

7. The granules according to claim 1, wherein the acrylate copolymer is an ammonio methacrylate copolymer.

8. The granules according to claim 1, wherein the granules comprise at least 85% w/w cholestyramine.

9. The granules according to claim 1, wherein the diameter of the granules is from 1000 µm to 1600 µm.

10. The granules according to claim 1, formulated for colon targeted delivery.

11. A multiparticulate drug delivery system comprising a plurality of cholestyramine granules according to claim 1.

12. The drug delivery system according to claim 11, wherein the cholestyramine granules are formulated for colon targeted delivery.

13. The drug delivery system according to claim 12, wherein the colon targeted delivery is based on an enzyme-controlled release.

14. The drug delivery system according to claim 12, wherein the colon targeted delivery is based on a pH- and diffusion-controlled release.

15. An oral formulation comprising
   i. a plurality of granules according to claim 1; and
   ii. a colon release coating around said granules.

16. The formulation according to claim 15, wherein the colon release coating is elastic.

17. The formulation according to claim 15, wherein the colon release coating comprises starch.

18. The formulation according to claim 17, wherein the starch is resistant starch type 2 (RS2).

19. The formulation according to claim 15, wherein the colon release coating comprises a diffusion-controlled inner coating layer and an enteric outer coating layer.

20. The formulation according to claim 19, wherein the diffusion-controlled inner coating layer comprises poly (ethyl acrylate-co-methyl methacrylate-co-trimethylammonioethyl methacrylate chloride) 1:2:0.2, 1:2:0.1 or a combination thereof.

21. The formulation according to claim 19, wherein the enteric outer coating layer comprises hydroxypropyl methylcellulose acetate succinate.

22. A method for treating or preventing bile acid malabsorption or bile acid diarrhoea in a patient in need thereof, the method comprising administering to the patient a therapeutically effective amount of a formulation according to claim 15.

23. The method according to claim 22, wherein the bile acid malabsorption is the result of ileal disease (Crohn's disease), ileal resection or ileal bypass, the result of overproduction of bile acids or defective feedback inhibition of hepatic bile acid synthesis, or the result of cholecystectomy, vagotomy, small intestinal bacterial overgrowth (SIBO), coeliac disease, pancreatic insufficiency (chronic pancreatitis, cystic fibrosis), pancreatic transplant, radiation enteritis, collagenous colitis, microscopic colitis, lymphocytic colitis, ulcerative colitis or irritable bowel syndrome (IBS-D).

24. The method according to claim 22, wherein the bile acid diarrhoea is bile acid diarrhoea following oral administration of an IBAT inhibitor.

25. The method according to claim 22, wherein the bile acid diarrhoea is bile acid diarrhoea following treatment of a cholestatic liver disease comprising oral administration of an IBAT inhibitor.

26. The method according to claim 25, wherein the IBAT inhibitor is
   1,1-dioxo-3,3-dibutyl-5-phenyl-7-methylthio-8-(N-{(R)-α-[N—((S)-1-carboxypropyl)-carbamoyl]-4-hydroxybenzyl}carbamoylmethoxy)-2,3,4,5-tetrahydro-1,2,5-benzothiadiazepine; or
   1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;
or a pharmaceutically acceptable salt thereof.

27. A population of granules, each granule comprising at least 70% w/w cholestyramine and
   i. a combination of at least 6% w/w of a binding agent and at least 2% w/w of an acrylate copolymer; or
   ii. a combination of at least 5% w/w of a binding agent and at least 3% w/w of an acrylate copolymer; or
   iii. a combination of at least 6% w/w of a binding agent, at least 1% w/w of an acrylate copolymer and from 5% to 15% w/w microcrystalline cellulose;
wherein the binding agent comprises a cellulose ether, a vinylpyrrolidone-based polymer, or a combination thereof; and
wherein the cholestyramine, the binding agent, the acrylate copolymer, and the microcrystalline cellulose, and a liquid are combined to form a wet mass that is dried and milled to form the population of granules.

* * * * *